(12) United States Patent
Coric et al.

(10) Patent No.: US 11,083,724 B2
(45) Date of Patent: *Aug. 10, 2021

(54) RIMEGEPANT FOR CGRP RELATED DISORDERS

(71) Applicant: Biohaven Pharmaceutical Holding Company Ltd., New Haven, CT (US)

(72) Inventors: Vladimir Coric, Madison, CT (US); Robert Croop, Newton Square, PA (US)

(73) Assignee: Biohaven Pharmaceutical Ireland DAC, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/884,196

(22) Filed: May 27, 2020

(65) Prior Publication Data

US 2020/0383969 A1 Dec. 10, 2020

Related U.S. Application Data

(63) Continuation of application No. 16/767,134, filed as application No. PCT/US2019/023940 on Mar. 25, 2019.

(60) Provisional application No. 62/647,794, filed on Mar. 25, 2018, provisional application No. 62/664,761, filed on Apr. 30, 2018, provisional application No. 62/774,285, filed on Dec. 2, 2018, provisional application No. 62/777,180, filed on Dec. 9, 2018, provisional application No. 62/777,625, filed on Dec. 10, 2018.

(51) Int. Cl.
| | | |
|---|---|---|
| *A61K 31/395* | (2006.01) | |
| *A61K 31/4709* | (2006.01) | |
| *A61K 9/20* | (2006.01) | |
| *A61P 25/06* | (2006.01) | |
| *A61K 31/4545* | (2006.01) | |

(52) U.S. Cl.
CPC ........ *A61K 31/4709* (2013.01); *A61K 9/2018* (2013.01); *A61K 9/2063* (2013.01); *A61K 31/4545* (2013.01); *A61P 25/06* (2018.01)

(58) Field of Classification Search
CPC .................................................. A61K 31/395
See application file for complete search history.

(56) References Cited

U.S. PATENT DOCUMENTS

| 6,709,669 | B1 | 3/2004 | Murray et al. |
|---|---|---|---|
| 6,890,472 | B2 | 5/2005 | Heath |
| 7,121,822 | B2 | 10/2006 | Heath |
| 7,704,583 | B2 | 4/2010 | Heath |
| 8,314,117 | B2 | 11/2012 | Luo et al. |
| 8,669,368 | B2 | 3/2014 | Leahy et al. |
| 8,759,372 | B2 | 6/2014 | Roberts et al. |
| 9,192,580 | B2 * | 11/2015 | Green ............... A61K 47/42 |
| 9,718,845 | B2 | 8/2017 | Leahy et al. |
| 2013/0225636 | A1 * | 8/2013 | Roberts ............ A61K 31/444 514/303 |
| 2018/0015085 | A1 | 1/2018 | Christopher et al. |
| 2021/0000814 | A1 * | 1/2021 | Coric ................. A61K 9/19 |

FOREIGN PATENT DOCUMENTS

| EP | 2815749 A1 | 12/2014 |
|---|---|---|
| GB | 1548022 A | 7/1979 |
| WO | 00/09313 A1 | 2/2000 |
| WO | 00/61117 A1 | 10/2000 |
| WO | 2011/046997 A1 | 4/2011 |
| WO | 2012/050764 A1 | 4/2012 |
| WO | 2013/130402 A1 | 9/2013 |

OTHER PUBLICATIONS

International Search Report dated Jun. 3, 2019 issued for the corresponding application PCT/US2019/023940 (3 pages).
Written Opinion dated Jun. 3, 2019 issued for the corresponding application PCT/US2019/023940 (7 pages).
Ho et al. "Randomized Controlled Trial of the CGRP Receptor Antagonist Telcagepant for Migraine Prevention" Neurology 2014, vol. 83, No. 11, pp. 958-966.
Marcus et al. "BMS-927711 for the Acute Treatment of Migraine: A Double-Blind, Randomized, Placebo Controlled, Dose-Ranging Trial" Cephalgia 2015, vol. 34, No. 2, pp. 114-125.
Connor et al. "Randomized, Controlled Trial of Telcagepant for the Acute Treatment of Migraine" Neurology 2009, vol. 73, pp. 970-977.
"Safety and Efficacy Study in Adult Subjects With Acute Migraines" Study NCT03235479 published by clinicaltrials.gov on Jul. 27, 2017, updated on May 23, 2018, and retrieved from https://www.clinicaltrials.gov/ct2/show/study/NCT03235479?term=NCT+03235479&draw=2&rank=1.
"Migraine: Developing Drugs for Acute Treatment, Guidance for Industry" Published by United States Food and Drug Administration in Feb. 2018 (12 pages).
Swan et al. "Pharmacokinetic Profile of Rizatriptan 10-mg Tablet and 10-mg Orally Disintegrating Tablet Administered With or Without Water in Healthy Subjects: An Open-Label, Randomized, Single-Dose, 3-Period Crossover Study" Journal of Clinical Pharmacology, 2006, 46, 172-178.
Maxalt®, Highlights of Prescribing Information, 17 pages (initial US approval: 1998).
Gladstone et al. "Newer Formulations of Triptanes: Advances in Migraine Management" Drugs, 2003, 63, 2285-2305.
Zomig®, Highlights of Prescribing Information, 29 pages (initial US approval: 1997).

\* cited by examiner

*Primary Examiner* — John S Kenyon

(57) ABSTRACT

Disclosed are methods of treating CGRP related disorders, e.g., migraine, by administering to a patient in need thereof rimegepant or a pharmaceutically acceptable salt thereof. Pharmaceutical compositions comprising rimegepant and kits including the pharmaceutical compositions and instructions are also disclosed.

20 Claims, 6 Drawing Sheets

RIMEGEPANT FOR CGRP RELATED DISORDERS

CROSS-REFERENCE TO RELATED APPLICATIONS

This application is a continuation of U.S. application Ser. No. 16/767,134 filed May 27, 2020, which is a national stage application under 35 U.S.C. § 371 of International Application No. PCT/US2019/023940, filed Mar. 25, 2019, which claims priority to U.S. Provisional Application No. 62/647,794 filed Mar. 25, 2018, U.S. Provisional Application No. 62/664,761 filed Apr. 30, 2018, U.S. Provisional Application No. 62/774,285 filed Dec. 2, 2018, U.S. Provisional Application No. 62/777,180 filed Dec. 9, 2018, and U.S. Provisional Application No. 62/777,625 filed Dec. 10, 2018, and all the benefits accruing therefrom under 35 U.S.C. § 119, the disclosure of each of which applications is herein incorporated by reference in its entirety.

FIELD OF THE INVENTION

The present invention relates to the use of rimegepant and salts thereof for treating CGRP-related disorders such as migraine.

BACKGROUND OF THE INVENTION

Migraine is a chronic and debilitating disorder characterized by recurrent attacks lasting four to 72 hours with multiple symptoms, including typically one-sided, pulsating headaches of moderate to severe pain intensity that are associated with nausea or vomiting, and/or sensitivity to sound (phonophobia) and sensitivity to light (photophobia). Migraines are often preceded by transient neurological warning symptoms, known as auras, which typically involve visual disturbances such as flashing lights, but may also involve numbness or tingling in parts of the body. Migraine is both widespread and disabling. The Migraine Research Foundation ranks migraine as the world's third most prevalent illness, and the Global Burden of Disease Study 2015 rates migraine as the seventh highest specific cause of disability worldwide. According to the Migraine Research Foundation, in the United States, approximately 36 million individuals suffer from migraine attacks. While most sufferers experience migraine attacks once or twice per month, more than 4 million people have chronic migraine, defined as experiencing at least 15 headache days per month, of which at least eight are migraine, for more than three months. Others have episodic migraine, which is characterized by experiencing less than 15 migraine days per month. People with episodic migraine may progress to chronic migraine over time. Migraine attacks can last four hours or up to three days. More than 90% of individuals suffering from migraine attacks are unable to work or function normally during a migraine attack, with many experiencing comorbid conditions such as depression, anxiety and insomnia. Also, those suffering from migraine often have accompanying nausea and have an aversion to consuming food or liquids during an attack.

CGRP (calcitonin gene-related peptide) is a 37 amino acid neuropeptide, which belongs to a family of peptides that includes calcitonin, adrenomedullin and amylin. In humans, two forms of CGRP (a-CGRP and 13-CGRP) exist and have similar activities. They vary by three amino acids and exhibit differential distribution. At least two CGRP receptor subtypes may also account for differential activities. The CGRP receptor is located within pain-signaling pathways, intracranial arteries and mast cells and its activation is thought to play a causal role in migraine pathophysiology. For example, research and clinical studies have shown: serum levels of CGRP are elevated during migraine attacks, infusion of intravenous CGRP produces persistent pain in migraine sufferers and non-migraine sufferers, and treatment with anti-migraine drugs normalizes CGRP activity.

Possible CGRP involvement in migraine has been the basis for the development and clinical testing of a number of compounds, including for example, olcegepant (Boehringer Ingelheim, Ridgefield, Conn.), telcagepant (Merck Sharp & Dohme Corp., Kenilworth, N.J.), ubrogepant (Allergan plc, Dublin, Ireland), rimegepant (Biohaven Pharmaceutical Holding Company Ltd., New Haven, Conn.), galcanezumab (Eli Lilly and Company, Indianapolis, Ind.), fremanezumab (Teva Pharmaceutical Industries, Petah Tikva, Israel), eptinezumab (Alder Biopharmaceuticals, Inc., Bothell, Wash.), and erenumab (Amgen Inc., Thousand Oaks, Calif.). Another compound recently studies for treatment of migraine is lasmiditan (Eli Lilly and Company, Indianapolis, Ind.).

Currently, clinicians use a number of pharmacologic agents for the acute treatment of migraine. A study published by the American Headache Society in 2015 concluded that the medications deemed effective for the acute treatment of migraine fell into the following classes: triptans, ergotamine derivatives, non-steroidal anti-inflammatory drugs ("NSAIDs"), opioids and combination medications. The current standard of care for the acute treatment of migraine is prescription of triptans, which are serotonin 5-HT receptor agonists. Triptans have been developed and approved for the acute treatment of migraine over the past two decades. The initial introduction of triptans represented a shift toward drugs more selectively targeting the suspected pathophysiology of migraine. While triptans account for almost 80% of anti-migraine therapies prescribed at office visits by healthcare providers, issues such as an incomplete effect or headache recurrence remain important clinical limitations. In fact, only about 30% of patients from clinical trials are pain free at two hours after taking triptans. In addition, triptans are contraindicated in patients with cardiovascular disease, cerebrovascular disease, or significant risk factors for either because of potential systemic and cerebrovascular vasoconstriction from the 5-HT$_{1B}$-mediated effects. Also, according to a January 2017 study published in the journal Headache, an estimated 2.6 million migraine sufferers in the United States have a cardiovascular event, condition or procedure that limits the potential of triptans as a treatment option.

Accordingly, there remains a significant unmet medical need for the treatment of migraine that may provide enhanced patient benefits compared to existing therapies. In addition, CGRP receptor antagonists may be useful pharmacological agents for disorders that involve other CGRP disorders. In addition to migraine, such disorders may include cluster headache (Doods (2001) *Curr. Opin. Invest. Drugs* 2, 1261-1268; Edvinsson et al. (1994) *Cephalalgia* 14, 320-327); chronic tension type headache (Ashina et al. (2000) *Neurology* 14, 1335-1340); pain (Yu et al. (1998) *Eur. J Pharmacol.* 347, 275-282); chronic pain (Hulsebosch et al. (2000) *Pain* 86, 163-175); neurogenic inflammation and inflammatory pain (Holzer (1988) *Neuroscience* 24, 739-768; Delay-Goyet et al. (1992) *Acta Physiol. Scanda.* 146, 537-538; Salmon et al. (2001) *Nature Neurosci.* 4, 357-358); eye pain (May et al. (2002) *Cephalalgia* 22, 195-196), tooth pain (Awawdeh et al. (2002) *Int. Endocrin. J* 35, 30-36), non-insulin dependent diabetes mellitus (Molina et al. (1990) *Diabetes* 39, 260-265); vascular disorders; inflammation (Zhang et al. (2001) *Pain* 89, 265); arthritis, bronchial hyperreactivity, asthma, (Foster et al. (1992) *Ann. NY Acad. Sci.* 657, 397-404; Schini et al. (1994) *Am. J Physiol.* 267, H2483-H2490; Zheng et al. (1993) *J Viral.* 67, 5786-5791); shock, sepsis (Beer et al. (2002) *Crit. Care Med.* 30, 1794-1798); opiate withdrawal syndrome (Salmon et al. (2001) *Nature Neurosci.* 4, 357-358); morphine tolerance (Menard et al. (1996) *J Neurosci.* 16, 2342-2351); hot flashes in men and women (Chen et al. (1993) *Lancet* 342, 49; Spetz et al. (2001) *J Urology* 166, 1720-1723); allergic dermatitis (Wallengren (2000) *Contact Dermatitis* 43, 137-143); psoriasis; encephalitis, brain trauma, ischaemia, stroke, epilepsy, and neurodegenerative diseases (Rohrenbeck et al. (1999) *Neurobiol. Dis.* 6, 15-34); skin diseases (Geppetti and Holzer, Eds., Neurogenic Inflammation, 1996, CRC Press, Boca Raton, Fla.), neurogenic cutaneous redness, skin rosaceousness and erythema; tinnitus (Herzog et al. (2002) *J Membr. Biol.* 189, 225); obesity (Walker et al. (2010) *Endocrinology* 151, 4257-4269); inflammatory bowel disease, irritable bowel syndrome, (Hoffman et al. (2002) *Scand. J Gastroenterol.* 37, 414-422) and cystitis.

SUMMARY OF THE INVENTION

The present invention is directed, among other things, to the treatment of CGRP related disorders, e.g., migraine, with rimegepant and salts thereof. By virtue of the present invention, it may now be possible to provide more effective GCRP related treatments to patients. Patients suffering from migraine may experience an improved response in one or more areas including, for example, fewer migraine headaches, improvements in pain freedom or freedom from most bothersome symptoms.

In one aspect of the invention, there is provided a method of treating migraine in a patient in need thereof, comprising administering to the patient a pharmaceutical composition comprising a therapeutically effective amount of rimegepant, or a pharmaceutically acceptable salt thereof, in order to provide decrease in the number of migraines per month for said patient of at least 20%.

In one aspect of the invention, the decrease in the number of migraines per month for said patient of at least 30%. in one aspect of the invention, the decrease in the number of migraines per month for said patient of at least 40%.

In one aspect of the invention, there is provided a method of treating migraine in a patient in need thereof, comprising administering to the patient a pharmaceutical composition comprising a therapeutically effective amount of rimegepant, or a pharmaceutically acceptable salt thereof, in order to provide Pain Freedom of the pharmaceutical composition of at about 30% greater than placebo.

In one aspect of the invention, the Pain Freedom is at least about 50% greater than placebo. In one aspect of the invention, the Pain Freedom of the pharmaceutical composition is from about 30-75% greater than placebo. In one aspect of the invention, the Pain Freedom is from about 35-65% greater than placebo.

In one aspect of the invention, there is provided a method of treating migraine in a patient in need thereof, comprising administering to the patient a pharmaceutical composition comprising a therapeutically effective amount of rimegepant, or a pharmaceutically acceptable salt thereof, in order to provide Freedom from MBS of the pharmaceutical composition of at about 30% greater than placebo.

In one aspect of the invention, the Freedom from MBS is at least about 40% greater than placebo. In one aspect of the invention, the Freedom from MBS is from about 30-50% greater than placebo. In one aspect of the invention, the Freedom from MBS is from about 35-65% greater than placebo.

In one aspect of the invention, the method provides an $AUC_{0-t}$ of from about 80-125% of 5000 (hr*ng/mL). In one aspect of the invention, the method provides an $AUC_{0-t}$ of from about 85-115% of 5000 (hr*ng/mL). In one aspect of the invention, the method provides an $AUC_{0-t}$ of from about 90-105% of 5000 (hr*ng/mL).

In one aspect of the invention, the method provides a $C_{max}$ of from about 80-125% of 835 (ng/mL). In one aspect of the invention, the method provides a $C_{max}$ of from about 85-120% of 835 (ng/mL). In one aspect of the invention, the method provides a $C_{max}$ of from about 95-115% of 835 (ng/mL).

In one aspect of the invention, the pharmaceutical composition is administered by oral, sublingual or buccal administration.

In one aspect of the invention, the pharmaceutical composition comprises from about 10 to 600 mg of rimegepant or a pharmaceutically acceptable salt thereof. In one aspect of the invention, the pharmaceutical composition comprises from about 25 to 300 mg of rimegepant or a pharmaceutically acceptable salt thereof. In one aspect of the invention, the pharmaceutical composition comprises from about 25 to 150 mg of rimegepant or a pharmaceutically acceptable salt thereof. In one aspect of the invention, the pharmaceutical composition comprises from about 50 to 100 mg of rimegepant or a pharmaceutically acceptable salt thereof. In one aspect of the invention, the pharmaceutical composition comprises from about 70 to 80 mg of rimegepant or a pharmaceutically acceptable salt thereof. In one aspect of the invention, the pharmaceutical composition comprises about 75 mg of rimegepant or a pharmaceutically acceptable salt thereof. In one aspect of the invention, the pharmaceutical composition comprises about 150 mg of rimegepant or a pharmaceutically acceptable salt thereof. In one aspect of the invention, the pharmaceutical composition comprises about 37.5 mg of rimegepant or a pharmaceutically acceptable salt thereof.

In one aspect of the invention, the rimegepant is in the form of a hemisulfate sesquihydrate salt.

In one aspect of the invention, there is provided a pharmaceutical composition comprising a therapeutically effective amount of rimegepant, or a pharmaceutically acceptable salt thereof, in order to provide an $AUC_{0-t}$ of from about 80-125% of 5000 (hr*ng/mL).

In one aspect of the invention, there is provided a pharmaceutical composition comprising a therapeutically effective amount of rimegepant, or a pharmaceutically acceptable salt thereof, in order to provide a $C_{max}$ of from about 80-125% of 835 (ng/mL).

In one aspect of the invention, the pharmaceutical composition is provided in the form of a tablet. In one aspect of the invention, the pharmaceutical composition comprises from about 50-60 wt % rimegepant hemisulfate sesquihydrate, about 30-35 wt % microcrystalline cellulose, about 2-7 wt % hydroxypropyl cellulose, about 3-7 wt % croscarmellose sodium, and about 0.1-1.0 wt % magnesium stearate. In one aspect of the invention, the pharmaceutical composition comprises about 57.1 wt % rimegepant hemisulfate sesquihydrate, about 33.4 wt % microcrystalline cellulose, about 4.0 wt % hydroxypropyl cellulose, about 5.0 wt % croscarmellose sodium, and about 0.5 wt % magnesium stearate.

In one aspect of the invention, the pharmaceutical composition is provided in the form of an oral solid molded fast-dispersing dosage form. In one aspect of the invention, the pharmaceutical composition comprises from about 70-80 wt % rimegepant hemisulfate sesquihydrate, about 10-20 wt % fish gelatin, about 10-20 wt % of a filler, and 0.1-5.0 wt % of a flavorant. In one aspect of the invention, the filler is mannitol.

In one aspect of the invention, there is provided a method of treating a condition associated with aberrant levels of CGRP in a patient in need thereof, comprising administering to the patient a pharmaceutical composition comprising a therapeutically effective amount of rimegepant, or a pharmaceutically acceptable salt thereof, in order to provide an $AUC_{0-t}$ of from about 80-125% of 5000 (hr*ng/mL).

In one aspect of the invention, there is provided a method of treating a condition associated with aberrant levels of CGRP in a patient in need thereof, comprising administering to the patient a pharmaceutical composition comprising a therapeutically effective amount of rimegepant, or a pharmaceutically acceptable salt thereof, in order to provide a $C_{max}$ of from about 80-125% of 835 (ng/mL). In one aspect of the invention, the disorder is selected from: migraine and cluster headache; chronic tension type headache; chronic pain; neurogenic inflammation and inflammatory pain; eye pain; tooth pain; non-insulin dependent diabetes mellitus; vascular disorders; inflammation; arthritis; bronchial hyperreactivity; asthma; shock; sepsis; opiate withdrawal syndrome; morphine tolerance; hot flashes in men and women; allergic dermatitis; psoriasis; encephalitis, brain trauma, ischaemia, stroke, epilepsy, and neurodegenerative diseases; skin diseases; neurogenic cutaneous redness, skin rosaceousness and erythema; tinnitus; obesity; inflammatory bowel disease; irritable bowel syndrome; and cystitis.

In one aspect of the invention, there is provided a kit for treating a condition associated with aberrant levels of CGRP in a patient, the kit comprising:

(a) a pharmaceutical composition comprising a therapeutically effective amount of rimegepant, or a pharmaceutically acceptable salt thereof;

(b) instructions for administering the pharmaceutical composition;

wherein the therapeutically effective amount provides an $AUC_{0-t}$ of from about 80-125% of 5000 (hr*ng/mL).

DETAILED DESCRIPTION OF THE INVENTION

Figure 1:
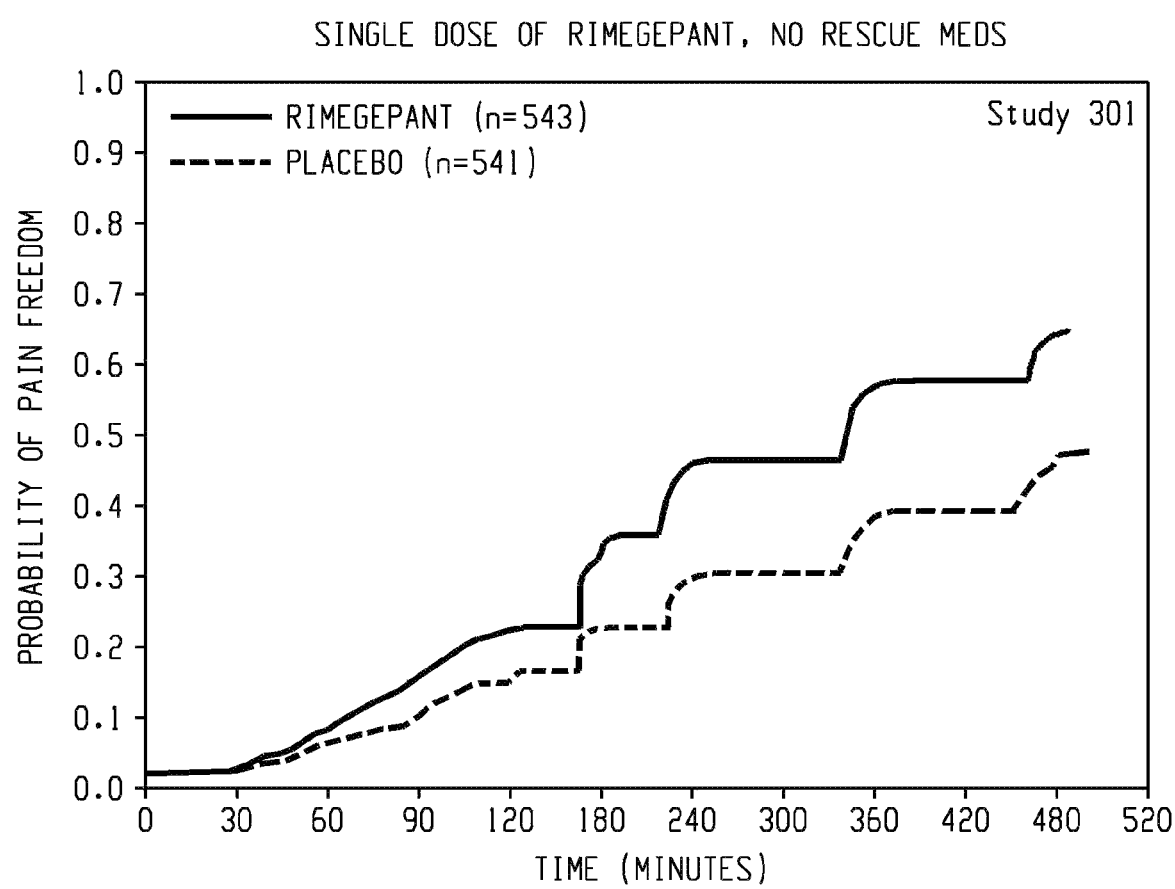
FIG. 1 shows the probability of pain freedom versus time in a clinical study entitled BHV3000-301: Phase 3: Double-Blind, Randomized, Placebo-Controlled, Safety and Efficacy Trial of BHV-3000 (Rimegepant) for the Acute Treatment of Migraine (ClinicalTrials.gov Identifier: NCT03235479).

The following detailed description is provided to aid those skilled in the art in practicing the present invention. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting.

As used in this application, except as otherwise expressly provided herein, each of the following terms shall have the meaning set forth below. Additional definitions are set forth throughout the application. In instances where a term is not specifically defined herein, that term is given an art-recognized meaning by those of ordinary skill applying that term in context to its use in describing the present invention.

The articles "a" and "an" refer to one or to more than one (i.e., to at least one) of the grammatical object of the article unless the context clearly indicates otherwise. By way of example, "an element" means one element or more than one element.

The term "about" refers to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 1%, 5%, 10% or 20% (i.e., ±10% or ±20%) depending on the context of the application. For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" should be assumed to be within an acceptable error range for that particular value or composition.

The term "administering" refers to the physical introduction of a composition comprising a therapeutic agent to a subject, using any of the various methods and delivery systems known to those skilled in the art. Administering can also be performed, for example, once, a plurality of times, and/or over one or more extended periods and can be a therapeutically effective dose or a subtherapeutic dose.

The term "AUC" (area under the curve) refers to a total amount of drug absorbed or exposed to a subject. Generally, AUC may be obtained from mathematical method in a plot of drug concentration in the subject over time until the concentration is negligible. The term "AUC" could also refer to partial AUC at specified time intervals.

The term "Cmax" refers to a maximum concentration of a drug in blood, serum, a specified compartment or test area of a subject between administration of a first dose and administration of a second dose. The term Cmax could also refer to dose normalized ratios, if specified.

The term "dosing interval," refers to the amount of time that elapses between multiple doses of a formulation disclosed herein being administered to a subject. Dosing interval can thus be indicated as ranges.

The term "dosing frequency" refers to the frequency of administering doses of a formulation disclosed herein in a given time. Dosing frequency can be indicated as the number of doses per a given time, e.g., once a week or once in two weeks.

The terms "in combination with" and "in conjunction with" refer to administration of one treatment modality in addition to another treatment modality. As such, "in combination with" or "in conjunction with" refers to administration of one treatment modality before, during, or after administration of the other treatment modality to the subject.

The term "pharmaceutically acceptable salt" refers to a salt form of one or more of the compounds described herein which are typically presented to increase the solubility of the compound in the gastric or gastroenteric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include, for example, those derived from alkali metals such as potassium and sodium, alkaline earth metals such as calcium, magnesium and ammonium salts, among numerous other acids and bases well known in the pharmaceutical art.

The terms "subject" and "patient" refer any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein.

The terms "effective amount", "therapeutically effective amount", "therapeutically effective dosage" and "therapeutically effective dose" of an agent (also sometimes referred to herein as a "drug") refers to any amount of the agent that, when used alone or in combination with another agent, protects a subject against the onset of a disease or promotes disease regression evidenced by a decrease in severity of disease symptoms, an increase in frequency and duration of disease symptom-free periods, or relief from impairment or disability due to the disease affliction. The therapeutically effective amount of an agent can be evaluated using a variety of methods known to the skilled practitioner, such as in human subjects during clinical trials, in animal model systems predictive of efficacy in humans, or by assaying the activity of the agent in in vitro assays.

The term "Tmax" refers to a time or period after administration of a drug when the maximum concentration (Cmax) is reached in blood, serum, a specified compartment or test area of a subject.

The term "treatment" refers to any treatment of a condition or disease in a subject and may include: (i) preventing the disease or condition from occurring in the subject which may be predisposed to the disease but has not yet been diagnosed as having it; (ii) inhibiting the disease or condition, i.e., arresting its development; relieving the disease or condition, i.e., causing regression of the condition; or (iii) ameliorating or relieving the conditions caused by the disease, i.e., symptoms of the disease. Treatment could be used in combination with other standard therapies or alone. Treatment or "therapy" of a subject also includes any type of intervention or process performed on, or the administration of an agent to, the subject with the objective of reversing, alleviating, ameliorating, inhibiting, slowing down or preventing the onset, progression, development, severity or recurrence of a symptom, complication or condition, or biochemical indicia associated with a disease.

With respect to headache, "treatment" is an approach for obtaining beneficial or desired results with a subject. For purposes of this invention, beneficial or desired clinical results include, but are not limited to, one or more of the following: improvement in any aspect of a headache including lessening severity, alleviation of pain intensity, and other associated symptoms, reducing frequency of recurrence, increasing the quality of life of those suffering from the headache, decreasing dose of other medications required to treat the headache and reducing the number of headache days per month. For migraine, other associated symptoms include, but are not limited to, nausea, vomiting, and sensitivity to light, sound, and/or movement. For cluster headache, other associated symptoms include, but are not limited to swelling under or around the eyes, excessive tears, red eye, Rhinorrhea or nasal congestion, and red flushed face.

For purposes of this disclosure, reference is made to the publication by the U.S. Food and Drug Administration (FDA), Guidance for Industry, "Migraine: Developing Drugs for Acute Treatment", February 2018, available from www.fda.gov/downloads/drugs/guidances/ucm419465.pdf. Terms used in the Examples, such as, for example, most bothersome symptoms (MBS) and Pain Freedom, are described in the FDA Guidance.

The starting materials useful for making the pharmaceutical compositions of the present invention are readily commercially available or can be prepared by those skilled in the art.

Rimegepant has the chemical formula, $C_{28}H_{28}F_2N_6O_3$ and the IUPAC name [(5S,6S,9R)-5-amino-6-(2,3-difluorophenyl)-6,7,8,9-tetrahydro-5H-cyclohepta[b]pyridin-9-yl] 4-(2-oxo-3H-imidazo[4,5-b]pyridin-1-yl)piperidine-1-carboxylate. Rimegepant is also referred to herein as BHV-3000.

The structure of rimegepant is:

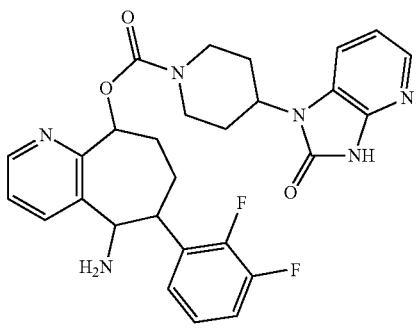 [SMILES: NC1c2cccnc2C(OC(=O)N2CCC(n3c(=O)[nH]c4ncccc43)CC2)CCC1c1cccc(F)c1F]

Rimegepant is described, for example in WO 2011/046997 published Apr. 21, 2011.

In a preferred aspect of the invention, rimegepant is present in the form of a hemisulfate sesquihydrate salt. This preferred salt form is described in WO 2013/130402 published Sep. 6, 2013.

The chemical formula of the salt form is $C_{28}H_{28}F_2N_6O_3 \cdot 0.5\ H_2SO_4 \cdot 1.5\ H_2O$ and the structure is as follows:

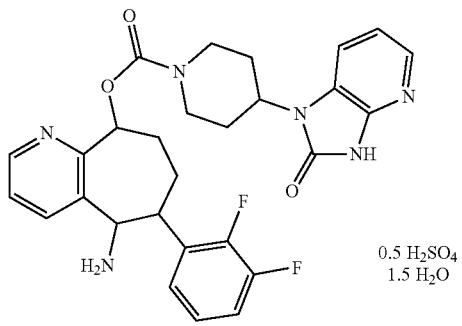 [SMILES: NC1c2cccnc2C(OC(=O)N2CCC(n3c(=O)[nH]c4ncccc43)CC2)CCC1c1cccc(F)c1F]

The pharmaceutical compositions of the present invention can be prepared in any suitable dosage form including, for example, such as tablets, capsules, nasal sprays, powders, granules, ointments, solutions, suppositories, injections, inhalants, gels, microspheres, and aerosols.

The pharmaceutical compositions of the present invention comprising rimegepant typically also include other pharmaceutically acceptable carriers (also referred to as excipients) such as, for example, binders, lubricants, diluents, coatings, disintegrants, barrier layer components, glidants, coloring agents, solubility enhancers, gelling agents, fillers, proteins, co-factors, emulsifiers, solubilizing agents, suspending agents, flavorants, preservatives and mixtures thereof. The choice of excipients depends on the desired characteristics of the compositions and on the nature of other pharmacologically active compounds in the formulation. Suitable excipients are known to those skilled in the art (see Handbook of Pharmaceutical Excipients, fifth edition, 2005 edited by Rowe et al., McGraw Hill).

Examples of pharmaceutically acceptable carriers that may be used in preparing the pharmaceutical compositions of the present invention may include, but are not limited to, fillers such as sugars, including lactose, sucrose, mannitol, or sorbitol; cellulose preparations such as maize starch, wheat starch, rice starch, potato starch, gelatin, gum tragacanth, methyl cellulose, hydroxypropyl methyl-cellulose, sodium carboxymethylcellulose, polyvinyl-pyrrolidone (PVP), talc, calcium sulphate, vegetable oils, synthetic oils, polyols, alginic acid, phosphate buffered solutions, emulsifiers, isotonic saline, pyrogen-free water and combinations thereof. If desired, disintegrating agents may be combined as well, and exemplary disintegrating agents may be, but not limited to, cross-linked polyvinyl pyrrolidone, agar, or alginic acid or a salt thereof such as sodium alginate. In an aspect of the invention, the flavoring agent is selected from mint, peppermint, berries, cherries, menthol and sodium chloride flavoring agents, and combinations thereof. In an aspect of the invention, the sweetener is selected from sugar, sucralose, aspartame, acesulfame, neotame, and combinations thereof.

In general, the pharmaceutical compositions of the present invention may be manufactured in conventional methods known in the art, for example, by means of conventional mixing, dissolving, granulating, dragee-making, levigating, emulsifying, encapsulating, entrapping, lyophilizing processes and the like.

In one aspect of the invention the pharmaceutical compositions are prepared in oral solid molded fast-dispersing dosage form, such as described in U.S. Pat. No. 9,192,580, issued Nov. 24, 2015.

The phrase "fast-dispersing dosage form" refers to compositions which disintegrate or disperse within 1 to 60 seconds, preferably 1 to 30 seconds, more preferably 1 to 10 seconds and particularly 2 to 8 seconds, after being placed in contact with a fluid. The fluid is preferably that found in the oral cavity, i.e., saliva, as with oral administration.

In a preferred embodiment, the compositions of the invention are solid fast-dispersing dosage forms comprising a solid network of the active ingredient, rimegepant, and a water-soluble or water-dispersible carrier containing fish gelatin. Accordingly, the carrier is inert towards the active ingredient. The network is obtained by subliming solvent from a composition in the solid state, the composition comprising the active ingredient and a solution of the carrier in the solvent. The dosage forms according to the invention can be prepared according to the process disclosed in Gregory et al., U.K. Patent No. 1,548,022 using fish gelatin as the carrier. Accordingly, an initial composition (or admixture) comprising the active ingredient and a solution of the fish gelatin carrier in a solvent is prepared followed by sublimation. The sublimation is preferably carried out by freeze drying the composition. The composition can be contained in a mold during the freeze-drying process to produce a solid form in any desired shape. The mold can be cooled using liquid nitrogen or solid carbon dioxide in a preliminary step prior to the deposition of the composition therein. After freezing the mold and composition, they are next subjected to reduced pressure and, if desired, controlled application of heat to aid in sublimation of solvent. The reduced pressure applied in the process can be below about 4 mm Hg, preferably below about 0.3 mm Hg. The freeze dried compositions can then be removed from the mold if desired or stored therein until later use.

When the process is used with active ingredients and fish gelatin as the carrier, a solid fast-dispersing dosage form is produced having the advantages associated with the use of fish gelatin described herein. Generally, fish gelatin is categorized as being from cold water and warm water fish sources and as being of the gelling or non-gelling variety. The non-gelling variety of fish gelatin, in comparison to gelling fish gelatin and bovine gelatin, contains lower proline and hydroxyproline amino acid content, which are known to be associated with cross-linking properties and gelling ability. Non-gelling fish gelatin can remain at solution concentrations of up to about 40% as well as in temperatures as low as 20° C. In one aspect of the invention, the fish gelatin used in accordance with the invention is preferably obtained from cold water fish sources and is the non-gelling type of fish gelatin. More preferably, in one aspect of the invention, the non-hydrolyzed form of non-gelling fish gelatin is used. In an alternative embodiment, spray-dried non-hydrolyzed non-gelling fish gelatin can be used. Fish gelatins suitable for use in the invention are commercially available.

The compositions according to the invention can also contain, in addition to the active ingredient arid fish gelatin carrier, other matrix forming agents and secondary components. Matrix forming agents suitable for use in the present invention include materials derived from animal or vegetable proteins, such as other gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

Other materials which may also be incorporated into the fast-dissolving compositions of the present invention include sugars such as mannitol, dextrose, lactose, galactose, and trehalose; cyclic sugars such as cyclodextrin; inorganic salts such as sodium phosphate, sodium chloride and aluminum silicates; and amino acids having from 2 to 12 carbon atoms such as glycine, L-alanine, L-aspartic acid, L-glutamic acid, L-hydroxyproline, L-isoleucine, L-leucine and L-phenylalanine. One or more matrix forming agents may be incorporated into the solution or suspension prior to solidification (freezing). The matrix forming agent may be present in addition to a surfactant or to the exclusion of a surfactant. In addition to forming the matrix, the matrix forming agent may aid in maintaining the dispersion of any active ingredient within the solution of suspension. This is especially helpful in the case of active agents that are not sufficiently soluble in water and must, therefore, be suspended rather than dissolved. Secondary components such as preservatives, antioxidants, surfactants, viscosity enhancers, coloring agents, flavoring agents, pH modifiers, sweeteners or taste-masking agents may also be incorporated into the fast-dissolving compositions. Suitable coloring agents include red, black and yellow iron oxides and FD & C dyes such as FD&C Blue No. 2 and FD&C Red No. 40 available from Ellis & Everard. Suitable flavoring agents include mint, raspberry, licorice, orange, lemon, grapefruit, caramel, vanilla, cherry and gr'ape flavors and combinations of these. Suitable pH modifiers include the edible acids and bases, such as citric acid, tartaric acid, phosphoric acid, hydrochloric acid, maleic acid and sodium hydroxide. Suitable sweeteners include, for example, sucralose, aspartame, acesulfame K and thaumatin. Suitable taste-masking agents include, for example, sodium bicarbonate, ion exchange resins, cyclodextrin inclusion compounds, adsorbates or microencapsulated actives.

Typical routes of administering the pharmaceutical compositions of the invention include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion technique. Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000).

Solid compositions are normally formulated in dosage units providing from about 1 to about 1000 mg of the active ingredient per dose. Some examples of solid dosage units are 0.1 mg, 1 mg, 10 mg, 37.5 mg, 75 mg, 100 mg, 150 mg, 300 mg, 500 mg, 600 mg and 1000 mg. Typical dose ranges in accordance with the present invention include from about 10-600 mg, 25-300 mg, 25-150 Mg, 50-100 mg, 60-90 mg, and 70-80 mg. Liquid compositions are generally in a unit dosage range of 1-100 mg/mL. Some examples of liquid dosage units are 0.1 mg/mL, 1 mg/mL, 10 mg/mL, 25 mg/mL, 50 mg/mL, and 100 mg/mL.

In some embodiments, a method may comprise administering to a subject one or more additional agent(s) simultaneously or sequentially with the rimegepant. In some embodiments, an additional agent may be an anti-headache medication such as an example anti-headache medication (e.g., 5-HT1 agonists, triptans, ergot alkaloids, opiates, adrenergic antagonists, NSAIDs or antibodies) known in the art. In some embodiments, a therapeutic effect may be greater as compared to use of rimegepant or one or more additional agent(s) alone. Accordingly, a synergistic effect between rimegepant and the one or more additional agents may be achieved. In some embodiments, the one or more additional agent(s) may be taken by a subject prophylactically.

In addition to migraine, other CGRP related disorders that may be treated by the pharmaceutical compositions and methods of the present invention include, for example, cluster headache; chronic tension type headache; chronic pain; neurogenic inflammation and inflammatory pain; eye pain; tooth pain; non-insulin dependent diabetes mellitus; vascular disorders; inflammation; arthritis; bronchial hyperreactivity; asthma; shock; sepsis; opiate withdrawal syndrome; morphine tolerance; hot flashes in men and women; allergic dermatitis; psoriasis; encephalitis, brain trauma, ischaemia, stroke, epilepsy, and neurodegenerative diseases; skin diseases; neurogenic cutaneous redness, skin rosaceousness and erythema; tinnitus; obesity; inflammatory bowel disease; irritable bowel syndrome; and cystitis.

In one aspect, the invention also provides kits for use in the instant methods. Kits can include one or more containers comprising a pharmaceutical composition described herein and instructions for use in accordance with any of the methods described herein. Generally, these instructions comprise a description of administration of the pharmaceutical composition to treat, ameliorate or prevent headache (such as migraine), or other CRGP disorder, according to any of the methods described herein. The kit may, for example, comprise a description of selecting an individual suitable for treatment based on identifying whether that individual has headache or whether the individual is at risk of having headache. The instructions are typically provided in the form of a package insert, or label, in accordance with the requirements of the regulatory having authority over the jurisdiction where the pharmaceutical composition is to be provided to patients.

In accordance with the present invention, administration of the pharmaceutical compositions comprising rimegepant to a subject may promote a reduction in severity (which can include reducing need for and/or amount of (e.g., exposure to) other drugs' and/or therapies generally used for this condition, including, for example, ergotamine, dihydroergotamine, or triptans for migraine), duration, and/or frequency (including, for example, delaying or increasing time to next episodic attack in an individual).

In addition, administration of the pharmaceutical compositions comprising rimegepant to a subject may promote a lessening or improvement of one or more symptoms of headache, or a reduction in the duration of a symptom, as compared to not administering a treatment.

In addition, administration of the pharmaceutical compositions comprising rimegepant to a subject may promote a reduction in the frequency of headache attacks in an individual (as compared to the level before treatment) in a certain time period, e.g., per month. For example, the frequency of attacks may be reduced by at least about any of 10%, 20%, 30%, 40%, 50%, 60%, or 70% in the individual as compared to the level before treatment.

In addition, administration of the pharmaceutical compositions comprising rimegepant to a subject may promote a delay in the development of headache, i.e., to defer, hinder, slow, retard, stabilize, and/or postpone progression of the disease. This delay can be of varying lengths of time, depending on the history of the disease and/or individuals being treated.

In addition, administration of the pharmaceutical compositions comprising rimegepant to a subject may delay the development or progression of a headache, i.e., delay of the initial manifestations and/or ensuing progression of the disorder. Development of headache can be detectable and assessed using standard clinical techniques as well known in the art. However, development also refers to progression that may be undetectable.

EXAMPLES

The following examples illustrate the invention and are not intended to limit the scope of the invention.

Example 1

Tablet Manufacture—A batch is prepared to manufacture tablets containing a dose of 75 mg of rimegepant as follows. The composition of the batch is set forth below in Table 1. Tablets are made from the batch as indicated.

TABLE 1

| Ingredient | Percent per Tablet | Amount per Tablet, (mg) | Amount per 100,000 Tablet Batch (g) |
|---|---|---|---|
| Intra-granular | | | |
| Rimegepant (as hemisulfate sesquihydrate equivalent to 75 mg as base) | 57.11 | 85.67 | 8575.5 |
| Microcrystalline cellulose, NF | 13.39 | 20.09 | 2,011.0 |
| Hydroxypropyl Cellulose), USP/NF (Klucel EXF PHARM) | 4.00 | 6.00 | 600.6 |
| Croscarmellose Sodium NF | 2.50 | 3.75 | 375.4 |
| Purified Water USP | q.s. | N/A | 0[1] |
| Intragranular Dispensed Solids | | | 11562 |
| Extra-granular | | | |
| Microcrystalline cellulose NF | 20.00 | 30.00 | 3,003.0 |
| Croscarmellose Sodium NF | 2.50 | 3.75 | 375.4 |
| Magnesium Stearate NF | 0.50 | 0.75 | 75.08 |
| Total Core Tablet | 100.0 | 150 | 15015 |

[1]Purified Water is removed in-process. An excess amount is dispensed. The portion consumed is documented. Intragranular Dispensed Solids does not include water.

1. The rimegepant hemisulfate sesquihydrate and all excipients are weighed.
2. Pass the rimegepant hemisulfate sesquihydrate, microcrystalline cellulose (intragranular portion), hydroxypropyl cellulose, and croscarmellose sodium (intragranular portion) through a 20-mesh screen.
3. Load the sieved mixture from 2 into a suitable granulator equipped with an appropriate size bowl & dry mix for 10 minutes. Set impeller speed to low & turn chopper off.
4. While mixing, equip the granulator with a spray tip and add purified water until endpoint is reached.
5. Mix wet mass for 30 seconds with impeller set to low and chopper set to low.
6. Discharge the wet mass into expansion chamber of fluid bed dryer. Dry to target LOD of <2%.
7. Mill the dried granules using the Comil with an appropriate screen (0.075R) and spacer (0.050). Perform bulk and tapped density & particle size distribution analyses. Record results. Calculate Carr Index & Carr Index mean from two samples.
8. Calculate the fractional yield. Recalculate the extragranular quantities.
9. Pass the microcrystalline cellulose and croscarmellose through a 20-mesh screen.
10. Combine the milled granulation with the recalculated microcrystalline cellulose (extragranular portion), croscarmellose sodium (extragranular portion) in a 2-cubic foot tote & blend for 150 revolutions.
11. Pass the magnesium stearate through 30-mesh screen.
12. Add screened magnesium stearate to the 2 cubic foot tote contents & blend for 75 revolutions.
13. Collect blend uniformity samples per plan.
14. Perform bulk & tapped density and particle size analyses & calculate Carr Index.
15. Discharge into a suitable container and weigh.
16. Set up 716-station rotary tablet press with 7 mm round concave plain tooling. Adjust number of stations as needed.
17. Adjust the press to achieve the following specifications for the tablets: Friability of 5 0.3% loss; Hardness of 10-14 kP; Thickness of 3.60-4.10 mm; and Disintegration of 2:30 minutes.
18. Conduct in-process testing as follows:
    Tablet friability and disintegration at beginning, middle and end of run
    Tablet hardness, tablet thickness, individual tablet weights, average tablet weights, and appearance at 15 minute intervals
19. Pass the tablets through a de-duster and metal detector.
20. Package tablets in double polyethylene bags in a suitable container.

Example 2

Clinical Trial—BHV3000-301: Phase 3: Double-Blind, Randomized, Placebo-Controlled, Safety and Efficacy Trial of BHV-3000 (Rimegepant) for the Acute Treatment of Migraine (ClinicalTrials.gov Identifier: NCT03235479).

A phase 3 clinical study was conducted with 1490 participants, as follows.

Study Description

The purpose of this study was to compare the efficacy of BHV-3000 (rimegepant) versus placebo in subjects with Acute Migraines

| Condition or disease | Intervention/treatment |
|---|---|
| Migraine | Drug: BHV-3000 |
| Acute Migraine | Drug: Placebo Oral Tablet |
| Phonophobia | |
| Photophobia | |

Study Design
   Study Type: Interventional (Clinical Trial)
   Actual Enrollment: 1490 participants
   Allocation: Randomized
   Intervention Model: Parallel Assignment
   Intervention Model Description: Double-blind to Sponsor, Investigator and Subject Randomized Controlled Trial Masking: Triple (Participant, Care Provider, Investigator)
Masking Description: Double-blind to Sponsor, Investigator and Subject
Primary Purpose: Treatment
Official Title: BHV3000-301: Phase 3: Double-Blind, Randomized, Placebo-Controlled, Safety and Efficacy Trial of BHV-3000 (Rimegepant) for the Acute Treatment of Migraine
Arms and Interventions

| Arm | Intervention/treatment |
|---|---|
| Experimental: BHV-3000 | Drug: BHV-3000 75 mg tablet QD |
| Placebo Comparator: Placebo | Drug: Placebo Oral Tablet equivalent of 75 mg tablet QD |

Outcome Measures
Primary Outcome Measures:
1. Pain freedom of rimegepant (75 mg tablet) compared with placebo in the acute treatment of migraine will be measured using the number of evaluable subjects that report no pain at 2 hours post-dose. [Time Frame: Two hours post dose]
    Pain will be measured on a 4 point Likert scale (0=none, 1=mild, 2=moderate, 3=severe)
2. Freedom from the most bothersome symptom (MBS) of rimegepant (75 mg tablet) compared with placebo will be measured using the number of evaluable subjects that report the absence of their MBS at 2 hours post-dose. [Time Frame: Two hours post dose]
    The MBS (nausea, phonophobia or photophobia) will measured using a binary scale (0=absent, 1=present).
Secondary Outcome Measures:
1. To measure the difference between rimegepant (75 mg tablet) compared to placebo from 2 to 24 hours, using the number of subjects that do not experience any headache pain through the time period of interest. [Time Frame: 2 hours-24 hours post-dose]
    Sustained Pain Freedom as measured by a 4 point numeric rating scale (None, Mild, Moderate, Severe)
2. The difference between rimegepant (75 mg tablet) compared to placebo by tabulating the absence of photophobia at 2 hours post-dose in the subset of subjects that reported the presence of photophobia at headache baseline. [Time Frame: 2 hours post-dose]
    Photophobia
3. To evaluate rimegepant (75 mg tablet) compared to placebo by tabulating the number of subjects that report the absence of phonophobia at 2 hours post-dose in the subset of subjects that reported the presence of phonophobia at headache baseline. [Time Frame: 2 hours post-dose]
    Phonophobia
4. To measure the difference between rimegepant (75 mg tablet) compared to placebo on Pain Relief, at 2 hours post-dose, for those that report a pain level of moderate or severe at baseline and then report a pain level of none or mild. [Time Frame: 2 hours post-dose]
    Pain Relief as measured by a 4 point numeric rating scale (None, Mild, Moderate, Severe)
5. Freedom from Nausea by tabulating the number of subjects that report the absence of nausea at 2 hours post-dose in the subset of subjects that reported the presence of nausea at headache baseline. [Time Frame: 2 hours post-dose]
    Freedom from Nausea
6. The difference between rimegepant (75 mg tablet) compared to placebo on the probability of requiring rescue medication using the number of subjects that take rescue medication within 24 after administration of study medication (BHV3000 or placebo). [Time Frame: up to 24 hours post-dose]
    Requiring Rescue Medication
7. To measure the difference between rimegepant (75 mg tablet) compared to placebo on sustained pain freedom, from 2 to 48 hours, using the number of subjects that do not experience any headache pain through the time period of interest. [Time Frame: 2 hours-24 hours post-dose]
    Sustained Pain Freedom
8. Rimegepant (75 mg tablet) compared to placebo on sustained pain relief, from 2 to 24 hours by using the number of subjects that do not use any rescue medications, and do not experience any moderate or severe headache pain through that time. [Time Frame: 2 hours-24 hours post-dose]
    Sustained Pain Relief as measured by a 4 point numeric rating scale (None, Mild, Moderate, Severe)
9. To measure the difference between rimegepant (75 mg tablet) compared to placebo on sustained pain relief from 2 to 48 hours, using the number of subjects that do not use any rescue medications and do not experience moderate to severe headache pain. [Time Frame: 2 hours-48 hours post-dose]
    Sustained Pain Relief as measured by a 4 point numeric rating scale (None, Mild, Moderate, Severe)
10. To measure the difference between rimegepant (75 mg tablet) relative to placebo on the proportion of subjects able to function normally, at 2 hours, using the number of subjects that self-report as "normal" on the functional disability scale. [Time Frame: 2 hours post-dose]
    Functional Disability Score
11. To measure the difference between rimegepant (75 mg tablet) compared to placebo on pain relapse using the number of subjects that are pain free at 2 hours post-dose and then have a headache of any severity within 48 hours of study medication. [Time Frame: 2 hours to 48 hours post-dose]
    Pain relapse as measured by a 4 point numeric rating scale (None, Mild, Moderate, Severe)

Further details concerning the clinical study including eligibility criteria, contacts and locations and more information can be found at www.clinicaltrials.gov for ClinicalTrials.gov
    Identifier: NCT03235479.

Example 3

Clinical Trial—BHV3000-302: Phase 3: Double-Blind, Randomized, Placebo-Controlled, Safety and Efficacy Trial of BHV-3000 (Rimegepant) for the Acute Treatment of Migraine (ClinicalTrials.gov Identifier: NCT03237845)
A phase 3 clinical study was conducted with 1503 participants, as follows.
Study Description
Brief Summary:
The purpose of this study is to compare the efficacy of BHV-3000 (rimegepant) versus placebo in subjects with Acute Migraines

| Condition or disease | Intervention/treatment |
|---|---|
| Migraine<br>Acute Migraine<br>Phonophobia<br>Photophobia | Drug: BHV-3000<br>Drug: Placebo Oral Tablet |

Study Design
    Study Type: Interventional (Clinical Trial)
    Actual Enrollment: 1503 participants
    Allocation: Randomized
    Intervention Model: Parallel Assignment
    Intervention Model Description: Double-blind to Sponsor, Investigator and Subject
    Masking: Triple (Participant, Care Provider, Investigator)
    Masking Description: Double-blind to Sponsor, Investigator and Subject
    Primary Purpose: Treatment
    Official Title: BHV3000-302: Phase 3: Double-Blind, Randomized, Placebo-Controlled, Safety and Efficacy Trial of BHV-3000 (Rimegepant) for the Acute Treatment of Migraine
    Actual Study Start Date: Jul. 26, 2017
    Primary Completion Date: Jan. 25, 2018
    Study Completion Date: Jan. 31, 2018
Arms and Interventions

| Arm | Intervention/treatment |
|---|---|
| Experimental: BHV-3000<br>rimegepant 75 mg tablet QD | Drug: Rimegepant<br>active |
| Placebo Comparator: Placebo<br>Matching 75 mg placebo tablet QD | Drug: Placebo<br>placebo |

Outcome Measures
Primary Outcome Measures:
    1. Pain Freedom of rimegepant (75 mg tablet) compared with placebo in the acute treatment of migraine will be measured using the number of evaluable subjects that report no pain at 2 hours post-dose. [Time Frame: Two hours post dose]
        Pain will be measured on a 4 point Likert scale (0=none, 1=mild, 2=moderate, 3=severe)
    2. Freedom from the most bothersome symptom (MBS) of rimegepant (75 mg tablet) compared with placebo will be measured using the number of evaluable subjects that report the absence of their MBS at 2 hours post-dose. [Time Frame: Two hours post dose]
        The MBS (nausea, phonophobia or photophobia) will measured using a binary scale (0=absent, 1=present).
Secondary Outcome Measures:
    1. Rimegepant (75 mg tablet) compared to placebo from 2 to 24 hours, using the number of subjects that do not experience any headache pain through the time period of interest. [Time Frame: 2 hours-24 hours post-dose]
        Sustained Pain Freedom as measured by a 4 point numeric rating scale (None, Mild, Moderate, Severe)
    2. Rimegepant (75 mg tablet) compared to placebo by tabulating the number of subjects that report the absence of photophobia at 2 hours post-dose in the subset of subjects that reported the presence of photophobia at headache baseline. [Time Frame: 2 hours post-dose]
        Freedom from Photophobia
    3. Rimegepant (75 mg tablet) compared to placebo by tabulating the number of subjects that report the absence of phonophobia at 2 hours post-dose in the subset of subjects that reported the presence of phonophobia at headache baseline. [Time Frame: 2 hours post-dose]
        Freedom from Phonophobia
    4. To measure rimegepant (75 mg tablet) compared to placebo on Pain Relief, at 2 hours post-dose, that report a pain level of moderate or severe at baseline and then report a pain level of none or mild. [Time Frame: 2 hours post-dose]
        Pain Relief as measured by a 4 point numeric rating scale (None, Mild, Moderate, Severe)
    5. Freedom from Nausea will by tabulating the number of subjects that report the absence of nausea at 2 hours post-dose in the subset of subjects that reported the presence of nausea at headache baseline. [Time Frame: 2 hours post-dose]
        Freedom from Nausea
    6. To measure rimegepant (75 mg tablet) compared to placebo on the probability of requiring rescue medication will be assessed using the number of subjects that take rescue medication within 24 after administration of study medication (BHV3000 or placebo). [Time Frame: up to 24 hours post-dose]
        Requiring Rescue Medication
    7. Rimegepant (75 mg tablet) compared to placebo on sustained pain freedom, from 2 to 48 hours, will be measured using the number of subjects that do not experience any headache pain through the time period of interest. [Time Frame: 2 hours-48 hours post-dose]
        Sustained Pain Freedom as measured by a 4 point numeric rating scale (None, Mild, Moderate, Severe)
    8. Rimegepant (75 mg tablet) compared to placebo on sustained pain relief, from 2 to 24 hours by using the number of subjects that do not use any rescue medications, and do not experience any moderate or severe headache pain through that time. [Time Frame: 2 hours-24 hours post-dose]
        Sustained Pain Relief as measured by a 4 point numeric rating scale (None, Mild, Moderate, Severe)
    9. Rimegepant (75 mg tablet) compared to placebo on sustained pain relief from 2 to 48 hours, using the number of subjects that do not use any rescue medications and do not experience moderate to severe headache pain. [Time Frame: 2 hours-48 hours post-dose]
        Sustained Pain Relief as measured by a 4 point numeric rating scale (None, Mild, Moderate, Severe)
    10. Rimegepant (75 mg tablet) relative to placebo on the proportion of subjects able to function normally, at 2 hours, using the number of subjects that self-report as "normal" on the functional disability scale. [Time Frame: 2 hours post-dose]
        Functional Disability Score
    11. Rimegepant (75 mg tablet) compared to placebo on pain relapse will be measured using the number of subjects that are pain free at 2 hours post-dose and then have a headache of any severity within 48 hours of study medication. [Time Frame: 2 hours to 48 hours post-dose]
        Pain relapse as measured by a 4 point numeric rating scale (None, Mild, Moderate, Severe)
Further details concerning the clinical study including eligibility criteria, contacts and locations and more information can be found at www.clinicaltrials.gov for ClinicalTrials.gov Identifier: NCT03237845.

Example 4

Figure 2:
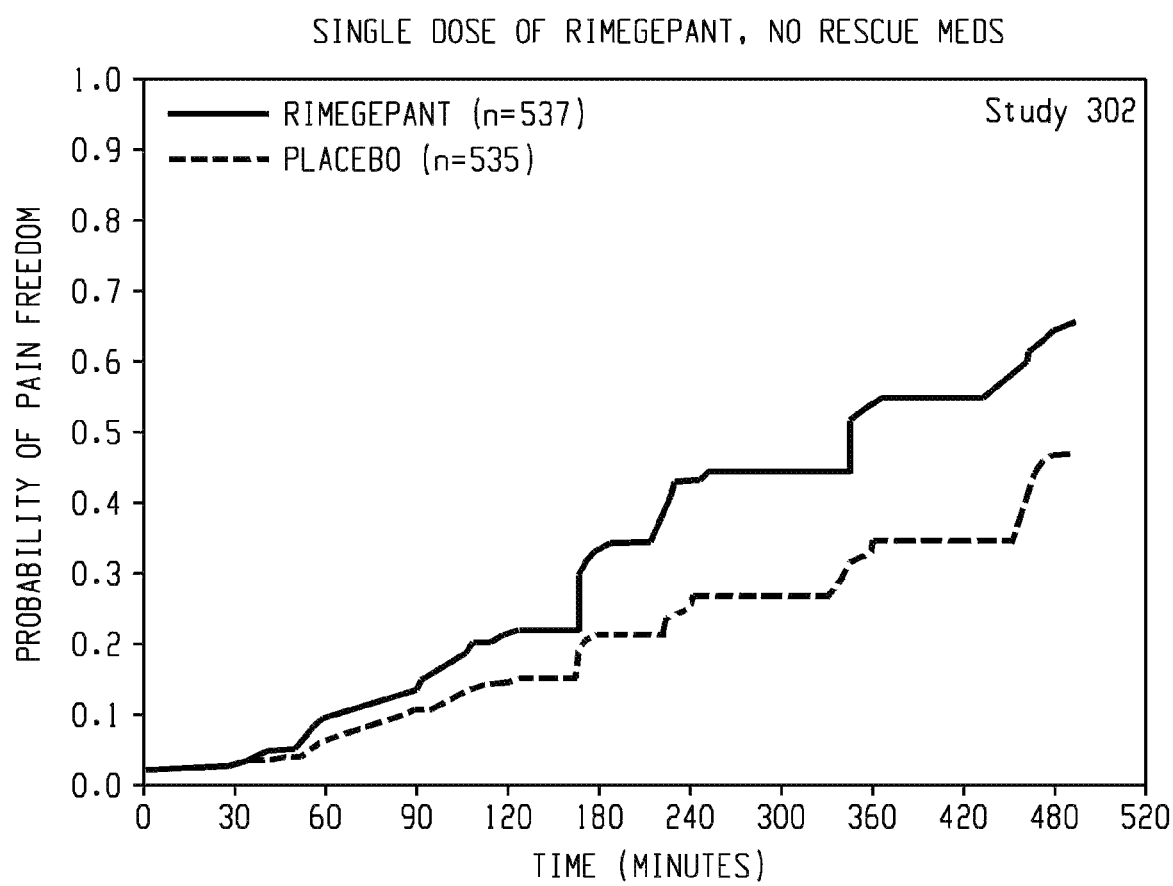
FIG. 2 shows the probability of pain freedom versus time in a clinical study entitled BHV3000-302: Phase 3: Double-Blind, Randomized, Placebo-Controlled, Safety and Efficacy Trial of BHV-3000 (Rimegepant) for the Acute Treatment of Migraine (ClinicalTrials.gov Identifier: NCT03237845).

Results from Clinical Trials—The study results from the clinical studies described in Example 2 and Example 3 are set forth in FIG. 1, FIG. 2 and Table 2, Table 3 and Table 4.

TABLE 2

Co-Primary Endpoints Met in Both Phase 3 Trials

Study 302

| 2 hour Endpoint | Rimegepant (N = 537) | Placebo (N = 535) | Adjusted p-value |
|---|---|---|---|
| Pain Freedom | 19.6% | 12.0% | <0.001 |
| Freedom from MBS[1] | 37.6% | 25.2% | <0.0001 |

Study 301

| 2 hour Endpoint | Rimegepant (N = 543) | Placebo (N = 541) | Adjusted p-value |
|---|---|---|---|
| Pain Freedom | 19.2% | 14.2% | <0.03 |
| Freedom from MBS[1] | 36.6% | 27.7% | <0.002 |

[1]Most Bothersome Symptom including Photophobia, Phonophobia or Nausea

TABLE 3

Pain Freedom: Increasing Benefit Over Time
Single Dose of Rimegepant, No Rescue Meds (Study 302)
Pain Freedom 2-8 Hours Post-Single Dosing with Rimegepant 75 mg

| Time Point (hours) | Percent (%) difference of Patients Pain Free: Rimegepant (n = 537) versus Placebo (n = 535) |
|---|---|
| 2 | 7 |
| 3 | 13 |
| 4 | 19 |
| 6 | 22 |
| 8 | 19 |

Data are Kaplan-Meier estimates of pain freedom; subjects were censored (not included) who took rescue medication or were lost to follow-up during the specified interval

TABLE 4

Pooled Liver Function Test (LET) Profile:
Rimegepant was Similar to Placebo in Both Studies
Complete Dataset of LFT Results from Study 301 and Study 302

| | Rimegepant (n = 1089) | Placebo (n = 1092) |
|---|---|---|
| ALT | | |
| >ULN | 22 (2.0%) | 24 (2.2%) |
| >3 × ULN | 1 (0.1%) | 1 (0.1%) |
| >5 × ULN | 0 | 0 |
| >10 × ULN | 0 | 0 |
| >20 × ULN | 0 | 0 |
| AST | | |
| >ULN | 12 (1.1%) | 16 (1.5%) |
| >3 × ULN | 1 (0.1%) | 0 |
| >5 × ULN | 0 | 0 |
| >10 × ULN | 0 | 0 |
| >20 × ULN | 0 | 0 |

*No bilirubin elevations > 2 × ULN across both Studies 301 and 302
*ALL CASES RESOLVED

Example 5

Bioequivalence—The bioequivalence of an oral solid molded fast-dispersing dosage form made with fish gelatin as described herein ("ODT") at a dose of 75 mg of rimegepant was compared to the 75 mg tablets used in the studies described in Examples 2 and 3.

The synopsis of the experiment is set forth below.

Primary Objective:

To compare the rate and extent of absorption of rimegepant ODT administered sublingually versus rimegepant tablet administered as 1×75 mg in healthy volunteers under fasting conditions.

Secondary Objective:

To assess the safety, tolerability, and PK of rimegepant tablet and ODT.

Exploratory Objective:

To compare the rate and extent of absorption of rimegepant ODT administered on top of the tongue versus rimegepant tablet administered as 1×75 mg in healthy volunteers under fasting conditions.

Study Design

This will be a single center, Phase 1, open-label, randomized study designed to be conducted as follows:

Part I: 4-period, 2-sequence, fully-replicated crossover bioequivalence study.

Part II: 2-period, 2-sequence, crossover relative bioavailability study. Part II may be conducted prior to Part I.

This study is intended for filing under Food and Drug Administration (FDA), European Medicines Agency (EMA), and Health Product and Food Branch (HPFB) regulations.

Each part of the study is intended to dose in one group; if, for any reason, either of the study parts is dosed in more than one group, all groups will be dosed at the same clinical site and the same protocol requirements and procedures will be followed within each group.

Sample Size

A total of approximately 60 healthy adult male or female volunteers will be dosed. Approximately 36 subjects will be included in the Part I bioequivalence portion of the study. Based on preliminary data from previous studies, the intra-subject coefficient of variation should be approximately 30% for both AUC and $C_{max}$. Thus, with this expected coefficient of variation and an expected ratio of AUC and $C_{max}$ within 0.91 and 1.10, the study should have a power of at least 80% to show bioequivalence with 30 subjects in a 4-period fully replicated design. In order of the study.

Approximately 24 subjects will be included in the Part II relative bioavailability portion of the study.

Confinements and Washouts

Part I

Subjects will be confined from at least 10 hours before drug administration of Period 1 until after the 72-hour post-dose blood draw of Period 4, i.e., until morning of Day 22.

There will be a washout period of 5 days or more between doses; subjects will remain confined in the clinic throughout the washout periods. Participation of each subject in this study should last approximately 3 weeks.

Part II

Subjects will be confined from at least 10 hours before drug administration of Period 1 until after the 72-hour post-dose blood draw of Period 2, i.e., until morning of Day 8.

There will be a washout period of 4 days or more between doses; subjects will remain confined in the clinic throughout the washout periods. Participation of each subject in this study should last approximately 1.5 weeks.

Randomization and Blinding

Subjects will be administered each treatment according to the 4-period, 2-sequence (CBCB or BCBC) and to the 2-period, 2-sequence (CA or AC), block randomization scheme produced by inVentiv for Part I and Part II, respectively. The randomization code will not be available to the Bioanalytical Division of inVentiv until the clinical and analytical phases of the study have been completed.

This study will be open-label due to the objective nature of the data.

Study Medication

Part I

Each subject will receive each of the 2 following treatments twice:

Treatment C (Test): 1×75 mg rimegepant sublingual ODT to be held under the tongue until fully dissolved then swallowed without water, administered under fasting conditions Treatment B (Reference): 1×75 mg rimegepant tablet swallowed with water, administered under fasting conditions Part II Each subject will receive each of the 2 following treatments once:

Treatment C (Test): 1×75 mg rimegepant sublingual ODT to be held under the tongue until fully dissolved then swallowed without water, administered under fasting conditions Treatment A (Reference): 1×75 mg rimegepant ODT to be held on top of the tongue until fully dissolved then swallowed without water, administered under fasting conditions Part I Treatment C One rimegepant ODT will be placed under each subject's tongue by the clinical staff and subject will be instructed not to swallow saliva until the ODT is completely dissolved. The subject will be instructed to give a hand sign once the ODT is completely dissolved and swallowed. A hand and mouth check will be performed to ensure consumption of the medication.

Time of dosing will be set to the time the ODT is placed under the tongue. No water will be allowed from 1 hour before dosing and until 1 hour post-dose. The complete dosing procedure must be completed within 2 minutes. If the ODT is not completely dissolved within 2 minutes, the subject will be asked to swallow with saliva and this will be documented. The start and end time of complete dosing will be recorded.

Treatment B

One rimegepant tablet will be administered to each subject with 240 mL of water and a hand and mouth check will be performed to ensure consumption of the medication.

Part II

Treatment C

One rimegepant ODT will be placed under each subject's tongue by the clinical staff and subject will be instructed not to swallow saliva until the ODT is completely dissolved. The subject will be instructed to give a hand sign once the ODT is completely dissolved and swallowed. A hand and mouth check will be performed to ensure consumption of the medication.

Time of dosing will be set to the time the ODT is placed under the tongue. No water will be allowed from 1 hour before dosing and until 1 hour post-dose. The complete dosing procedure must be completed within 2 minutes. If the ODT is not completely dissolved within 2 minutes, the subject will be asked to swallow with saliva and this will be documented. The start and end time of complete dosing will be recorded.

Treatment A

One rimegepant ODT will be placed on top of each subject's tongue by the clinical staff and subject will be instructed not to swallow saliva until the ODT is completely dissolved. The subject will be instructed to give a hand sign once the ODT is completely dissolved and swallowed. A hand and mouth check will be performed to ensure consumption of the medication.

Time of dosing will be set to the time the ODT is placed on the tongue. No water will be allowed from 1 hour before and until 1 hour post-dose. The complete dosing procedure must be completed within 2 minutes. If the ODT is not completely dissolved within 2 minutes, the subject will be asked to swallow with saliva and this will be documented. The start and end time of complete dosing will be recorded.

Sample Collection and Processing

In each period, a total of 17 blood samples will be drawn from each subject for pharmacokinetic analyses. Blood samples will be collected prior to drug administration and 0.083, 0.167, 0.333, 0.5, 0.667, 0.833, 1, 1.5, 2, 2.5, 5, 8, 12, 24, 48, and 72 hours post-dose (3 mL for each sampling time). The time tolerance window for blood sample collection will be ±29 seconds for all post-dose samples collected during the confinement period. Sample collections done outside the pre-defined time windows will not be considered as protocol deviations since actual post-dose sampling times will be used for pharmacokinetic and statistical analyses. Unless otherwise specified or for subject safety, when blood draws and other procedures coincide, blood draws will have precedence. A dead-volume intravenous catheter will be used for blood collection to avoid multiple skin punctures, when appropriate. Otherwise, blood samples will be collected by direct venipuncture.

The total volume of blood including that collected for eligibility, genotyping, and safety purposes should not exceed 308 mL for Part I and 185 mL for Part II.

Plasma samples will be collected and processed.

Pharmacokinetic and Statistical Analyses

PK analysis will be performed using Phoenix® WinNonlin®, which is validated for bioequivalence/bioavailability studies. Inferential statistical analyses will be performed using SAS® according to FDA, EMA, and HPFB guidelines.

Bioanalysis of all samples should be completed prior to the initiation of the pharmacokinetic and statistical analyses.

Pharmacokinetics

The following PK parameters will be calculated by standard non-compartmental methods for rimegepant:

$AUC_{0-t}$: area under the concentration-time curve from time zero to the last non-zero concentration $AUC_{0-inf}$: area under the concentration-time curve from time zero to infinity (extrapolated)

$C_{max}$: maximum observed concentration

Residual area: calculated as $100*(1-AUC_{0-t}/AUC_{0-inf})$ $T_{max}$: time of observed $C_{max}$ T½ el: elimination half-life Kel: elimination rate constant Additional PK analysis may be performed.

Safety Population

The safety population is defined as all subjects who received at least one dose of the study medication.

Pharmacokinetic Population

For Part I, the pharmacokinetic population will include all subjects completing at least 2 periods, including Treatment C and Treatment B, and for whom the pharmacokinetic profile can be adequately characterized.

For Part II, the pharmacokinetic population will include all subjects completing the study and for whom the pharmacokinetic profile can be adequately characterized.

Any subject with pre-dose concentrations will be presented in the concentrations and PK tables but excluded from descriptive statistics and inferential analyses (for the concerned period in Part I) if the pre-dose concentration is greater than 5% of the $C_{max}$ value measured for that subject.

Data from subjects who experienced emesis during the sampling interval and who were not withdrawn may be evaluated after completion of the PK analysis. Any subject who experienced emesis within 2 times median $T_{max}$ of rimegepant will be excluded from the statistical analysis (i.e., descriptive statistics and inferential analyses). Similarly, subjects withdrawn due to AEs or vomiting episodes will be presented in data listings but excluded from the statistical analysis tables (for the concerned period in Part I).

Statistical Analyses

A Statistical Analysis Plan (SAP) will be prepared after completion of the final protocol and finalized prior to database lock.

Demographic parameters will be summarized descriptively. Treatment-emergent adverse events (TEAEs) will be summarized descriptively by treatment for all subjects who were dosed (safety population). No inferential statistical analysis of safety data is planned.

Individual and mean plasma concentration versus time curves will be presented for both linear and semi-log scales. Descriptive statistics (arithmetic and geometric means, standard deviation [SD], coefficient of variation [CV %], minimum [Min], maximum [Max], and median) of the plasma concentrations and the PK parameters will be presented.

The results of the bioequivalence experiment are set forth in Table 5, Table 6 and Table 7.

TABLE 5

Summary Descriptive Statistics of BHV3000 for Pharmacokinetic Parameters by Treatment and Administration-Part I

| Analyte | Admin. | Treatment | Sequence | | AUC0_15 min (hr*ng/mL) | AUC0_30 min (hr*ng/mL) | AUC0_1 h (hr*ng/mL) | AUC0_2 h (hr*ng/mL) | AUC$_{0-t}$ (hr*ng/mL) | AUC$_{0-inf}$ (hr*ng/mL) | Residual area (%) | C$_{max}$ (ng/mL) | T$_{max}$ (hr) | T$_{1/2}$ (hr) | R$_{z1}$ (1/hr) |
|---|---|---|---|---|---|---|---|---|---|---|---|---|---|---|---|
| BHV3000 | 1 | Rimegepant ODT (Test) | | N | 34 | 34 | 34 | 34 | 34 | 34 | 34 | 34 | 34 | 34 | 34 |
| | | | | Mean | 3.33 | 48.61 | 316.30 | 1049.14 | 4973.13 | 4986.40 | 0.29 | 904.02 | 1.47 | 7.84 | 0.0921 |
| | | | | SD | 5.25 | 54.43 | 251.82 | 500.98 | 1429.06 | 1429.42 | 0.18 | 319.43 | 0.64 | 1.56 | 0.0190 |
| | | | | CV % | 157.92 | 111.96 | 79.61 | 47.75 | 28.74 | 28.57 | 63.45 | 35.34 | 43.30 | 19.93 | 20.6076 |
| | | | | Min | 0.00 | 0.00 | 1.28 | 301.45 | 2707.35 | 2717.72 | 0.09 | 292.92 | 0.67 | 5.75 | 0.0664 |
| | | | | Median | 0.95 | 25.58 | 280.40 | 1041.73 | 4539.82 | 4547.99 | 0.22 | 916.06 | 1.50 | 8.11 | 0.0855 |
| | | | | Max | 24.49 | 179.44 | 911.21 | 2171.04 | 8132.62 | 8147.14 | 1.06 | 1855.84 | 2.50 | 10.44 | 0.1205 |
| | | | | Geometric Mean | NC | NC | 181.16 | 927.52 | 4773.19 | 4787.03 | 0.25 | 849.54 | 1.34 | 7.68 | 0.0902 |
| BHV3000 | 2 | Rimegepant ODT (Test) | | N | 33 | 33 | 33 | 33 | 33 | 33 | 33 | 33 | 33 | 33 | 33 |
| | | | | Mean | 3.37 | 51.96 | 320.86 | 1030.22 | 5339.16 | 5354.99 | 0.31 | 915.87 | 1.54 | 8.69 | 0.0835 |
| | | | | SD | 4.44 | 35.31 | 242.39 | 532.43 | 1512.51 | 1514.60 | 0.16 | 308.35 | 0.70 | 1.83 | 0.0189 |
| | | | | CV % | 131.57 | 106.44 | 75.54 | 51.68 | 28.33 | 28.28 | 52.24 | 33.67 | 45.10 | 21.04 | 22.6469 |
| | | | | Min | 0.01 | 0.50 | 3.30 | 103.79 | 2344.91 | 2356.32 | 0.12 | 377.61 | 0.67 | 5.73 | 0.0540 |
| | | | | Median | 1.38 | 29.25 | 255.77 | 1082.04 | 5408.31 | 5421.88 | 0.25 | 920.80 | 1.50 | 8.54 | 0.0812 |
| | | | | Max | 18.95 | 210.33 | 753.99 | 2029.77 | 8855.17 | 8866.97 | 0.64 | 1529.91 | 2.50 | 12.84 | 0.1210 |
| | | | | Geometric Mean | 0.98 | 20.27 | 197.12 | 847.73 | 5125.96 | 5141.76 | 0.27 | 861.48 | 1.38 | 8.50 | 0.0816 |
| BHV3000 | 1 | Rimegepant Tablet (Ref) | | N | 34 | 34 | 34 | 34 | 34 | 34 | 34 | 34 | 34 | 34 | 34 |
| | | | | Mean | 0.68 | 19.87 | 232.43 | 924.82 | 5201.88 | 5215.35 | 0.28 | 907.50 | 2.04 | 7.98 | 0.0910 |
| | | | | SD | 0.88 | 19.95 | 186.00 | 514.84 | 1552.87 | 1552.78 | 0.16 | 366.37 | 1.24 | 1.73 | 0.0199 |
| | | | | CV % | 128.78 | 100.37 | 80.03 | 55.65 | 29.85 | 29.77 | 57.73 | 40.37 | 60.80 | 21.74 | 21.8434 |
| | | | | Min | 0.00 | 0.05 | 4.19 | 75.32 | 2635.48 | 2649.68 | 0.09 | 338.78 | 0.67 | 5.51 | 0.0603 |
| | | | | Median | 0.43 | 14.61 | 184.61 | 966.91 | 4838.68 | 4863.29 | 0.22 | 910.77 | 2.00 | 8.06 | 0.0860 |
| | | | | Max | 3.91 | 98.96 | 608.73 | 957.51 | 9551.84 | 9565.90 | 0.86 | 2204.05 | 5.00 | 11.50 | 0.1257 |
| | | | | Geometric Mean | NC | 9.51 | 139.80 | 743.54 | 4992.61 | 5006.58 | 0.24 | 841.03 | 1.75 | 7.79 | 0.0889 |
| BHV3000 | 2 | Rimegepant Tablet (Ref) | | N | 33 | 33 | 33 | 33 | 33 | 33 | 33 | 33 | 33 | 33 | 33 |
| | | | | Mean | 1.13 | 25.37 | 259.64 | 950.90 | 5493.72 | 5509.22 | 0.29 | 834.10 | 1.83 | 8.60 | 0.0833 |
| | | | | SD | 1.74 | 30.78 | 181.00 | 459.51 | 1670.65 | 1674.11 | 0.15 | 289.63 | 0.88 | 1.50 | 0.0164 |
| | | | | CV % | 154.86 | 121.33 | 69.71 | 48.32 | 30.41 | 30.39 | 50.78 | 34.72 | 48.30 | 17.39 | 19.6372 |
| | | | | Min | 0.00 | 0.29 | 5.44 | 84.31 | 2916.65 | 2936.35 | 0.12 | 386.15 | 0.67 | 5.89 | 0.0624 |
| | | | | Median | 0.31 | 11.41 | 226.97 | 889.26 | 5272.46 | 5293.49 | 0.28 | 798.82 | 1.50 | 8.49 | 0.0817 |
| | | | | Max | 6.89 | 121.36 | 732.48 | 2008.09 | 9819.52 | 9864.26 | 0.71 | 1671.55 | 5.00 | 11.10 | 0.1176 |
| | | | | Geometric Mean | NC | 11.38 | 186.64 | 811.29 | 5258.65 | 5274.04 | 0.26 | 785.69 | 1.64 | 8.46 | 0.0819 |

TABLE 6

Summary Descriptive Statistics of BHV3000 for Pharmacokinetic Parameters by Treatment-Part I

| Analyte | Treatment | | AUC0_15 min (hr*ng/mL) | AUC0_30 min (hr*ng/mL) | AUC0_1 h (hr*ng/mL) | AUC0_2 h (hr*ng/mL) | $AUC_{0-t}$ (hr*ng/mL) | $AUC_{0-inf}$ (hr*ng/mL) |
|---|---|---|---|---|---|---|---|---|
| BHV3000 | Rimegepant Sublingual ODT (Test) | N | 67 | 67 | 67 | 67 | 67 | 67 |
| | | Mean | 3.35 | 50.26 | 318.55 | 1039.82 | 5153.41 | 5167.94 |
| | | SD | 4.83 | 54.47 | 245.35 | 512.86 | 1471.15 | 1472.53 |
| | | CV % | 144.27 | 108.38 | 77.02 | 49.32 | 28.55 | 28.49 |
| | | Min | 0.00 | 0.00 | 1.28 | 103.79 | 2344.91 | 2356.32 |
| | | Median | 1.26 | 29.16 | 267.11 | 1082.04 | 4956.26 | 4963.67 |
| | | Max | 24.49 | 210.33 | 911.21 | 2171.04 | 8855.17 | 8866.97 |
| | | Geometric Mean | NC | NC | 188.85 | 887.32 | 4943.80 | 4958.58 |
| BHV3000 | Rimegepant ODT (Test) | N | 67 | 67 | 67 | 67 | 67 | 67 |
| | | Mean | 0.90 | 22.58 | 245.83 | 937.67 | 5345.62 | 5360.09 |
| | | SD | 1.38 | 25.81 | 182.67 | 484.74 | 1606.41 | 1608.21 |
| | | CV % | 153.46 | 114.29 | 74.31 | 51.70 | 30.05 | 30.00 |
| | | Min | 0.00 | 0.05 | 4.19 | 75.32 | 2635.48 | 2649.68 |
| | | Median | 0.34 | 14.03 | 218.33 | 899.23 | 5093.43 | 5104.27 |
| | | Max | 6.89 | 121.36 | 732.48 | 2008.09 | 9819.52 | 9864.26 |
| | | Geometric Mean | NC | 10.39 | 161.18 | 776.17 | 5121.92 | 5136.57 |

| Analyte | Treatment | | Residual area (%) | $C_{max}$ (ng/mL) | $T_{max}$ (hr) | $T_{1/2}$ (hr) | $K_d$ (1/hr) |
|---|---|---|---|---|---|---|---|
| BHV3000 | Rimegepant Sublingual ODT (Test) | N | 67 | 67 | 67 | 67 | 67 |
| | | Mean | 0.30 | 909.86 | 1.50 | 8.26 | 0.0879 |
| | | SD | 0.17 | 311.69 | 0.66 | 1.74 | 0.0193 |
| | | CV % | 57.53 | 34.26 | 44.00 | 21.07 | 21.9579 |
| | | Min | 0.09 | 292.92 | 0.67 | 5.73 | 0.0540 |
| | | Median | 0.24 | 920.80 | 1.50 | 8.39 | 0.0827 |
| | | Max | 1.06 | 1855.84 | 2.50 | 12.84 | 0.1210 |
| | | Geometric Mean | 0.26 | 855.40 | 1.36 | 8.07 | 0.0859 |
| BHV3000 | Rimegepant ODT (Test) | N | 67 | 67 | 67 | 67 | 67 |
| | | Mean | 0.29 | 871.35 | 1.94 | 8.28 | 0.0872 |
| | | SD | 0.15 | 330.38 | 1.08 | 0.64 | 0.0185 |
| | | CV % | 53.91 | 37.92 | 55.60 | 19.78 | 21.2192 |
| | | Min | 0.09 | 338.78 | 0.67 | 5.51 | 0.0603 |
| | | Median | 0.25 | 851.12 | 2.00 | 8.40 | 0.0825 |
| | | Max | 0.86 | 2204.05 | 5.00 | 11.50 | 0.1257 |
| | | Geometric Mean | 0.25 | 813.81 | 1.69 | 8.12 | 0.0854 |

TABLE 7

Ratios, 90% Geometric Confidence Intervals, $CV_{WR}$ (FDA Methodology)

| PK Parameter | Ratio[1] (%) | 90% Lower C.I.[2] (%) | 90% Upper C.I.[2] (%) | 95% Upper Confidence Bounds[3] (%) | $CV_{WR}$ (%) |
|---|---|---|---|---|---|
| $Ln(AUC_{0-t})$ | 96.79 | 92.63 | 101.15 | — | 15.70 |
| $Ln(AUC_{0-inf})$ | 96.81 | 92.66 | 101.14 | — | 15.68 |
| $Ln(C_{max})$ | 104.65 | 97.04 | 112.84 | — | 23.74 |

[1]Calculated using least-squares means according to the formula: $e^{(DIFFERENCE)} \times 100$.
[2]90% Geometric Confidence Interval using ln-transformed data.
[3]Reference Scaled ABE approach.

Example 6

Efficacy of Rimegepant—Results and analysis from the Clinical Trial—BHV3000-301 described in Example 2.

Objectives

To compare the efficacy, safety, and tolerability of rimegepant 75 mg oral tablet with placebo in the acute treatment of migraine in adults.

Methods

In a double-blind, randomized, placebo-controlled, multicenter study (Study 301, NCT03235479) adults≥18 years of age with at least a 1-year history of ICHD 3-beta migraine were eligible to participate. Following a 3- to 28-day screening period, subjects were randomized to receive rimegepant 75 mg or matching placebo and instructed to treat a single migraine attack with 1 dose of the blinded study drug (rimegepant or placebo) when headache pain reached moderate or severe intensity. The coprimary endpoints were pain freedom at 2 hours postdose and freedom from the most bothersome symptom (MBS) at 2 hours postdose. Safety assessments included adverse events (AEs), ECGs, vital signs, physical measurements, and routine laboratory tests, including assessment of liver function. Unless stated otherwise, values presented are mean±SD.

Results

In total, 1162 subjects were randomized to receive rimegepant (n=582) or placebo (n=580), and 1084 were evaluated for efficacy (rimegepant n=543, placebo n=541). Subjects had a mean age of 41.6±12.2 years, 85.5% were female, and by history had 4.7±1.8 attacks per month. At 2 hours postdose, rimegepant treated patients had higher pain-free rates than placebo treated patients (19.2% vs 14.2%, P=0.0298), were more likely to be free of the MBS (36.6% vs 27.7%, P=0.0016); and had higher rates of pain relief (56.0% vs 45.7%, P=0.0006). A single dose of rimegepant, without the use of rescue medication, demonstrated superiority versus placebo for sustained pain freedom and pain relief from 2 through 48 hours postdose (P=0.013 and P=0.0003, respectively). On a measure of functional disability, a greater proportion of rimegepant-treated patients achieved normal function at 2 hours (P<0.0001).

The safety and tolerability profiles of rimegepant were similar to placebo. The most common AEs were nausea (0.9%, 5/546 vs 1.1%, 6/549) and dizziness (0.7%, 4/546 vs 0.4%, 2/549). Serum ALT or AST levels greater than the upper limit of normal (ULN) were seen in 2.0% (11/546) and 3.6% (20/549) of subjects treated with rimegepant and placebo, respectively. One subject in the rimegepant group (0.2%) and 1 subject in the placebo group (0.2%) had a transaminase level>3 times ULN, and no subject in either group had a level>5 times ULN. No bilirubin elevations>2 times ULN were observed. Serious AEs (SAEs) were observed in 0.4% (n=2) of subjects in the rimegepant group and 0.2% (n=1) in the placebo group. No SAE was determined to be related to the study drug. Both subjects with SAEs in the rimegepant group had not been dosed before onset of the SAEs.

Conclusions

Significant and durable clinical effects were seen with a single dose of rimegepant across multiple outcome measures, including pain freedom, freedom from MBS, pain relief, and recovery of normal function. Rimegepant 75 mg oral tablet demonstrated favorable tolerability and safety, including a liver safety profile similar to placebo. These clinically meaningful results complement the benefits seen in an identical Phase 3 study (Study 302) and a previous Phase 2b study. Rimegepant may ultimately offer patients a novel approach for the acute treatment of migraine.

| Endpoints | Rimegepant 75 mg | Placebo | P-value[a] |
|---|---|---|---|
| Coprimary | | | |
| Pain-free at 2 hours | 19.2% [104/543] | 14.2% [77/541] | .0298 |
| Free from MBS at 2 hours | 36.6% [199/543] | 27.7% [150/541] | .0016 |
| Selected secondary | | | |
| Photophobia-free at 2 hours | 34.9% [164/470] | 24.8% [120/483] | .0005 |
| Phonophobia-free at 2 hours | 38.6% [133/345] | 30.9% 113/366] | .0299 |
| Pain relief at 2 hours | 56.0% [304/543] | 45.7% [247/541] | .0006 |
| Nausea-free at 2 hours | 46.9% [149/318] | 41.6% [134/322] | .1815 |
| Sustained pain relief, 2-24 hours | 38.9% [211/543] | 27.9% [151/541] | .0001 |

Figure 3:
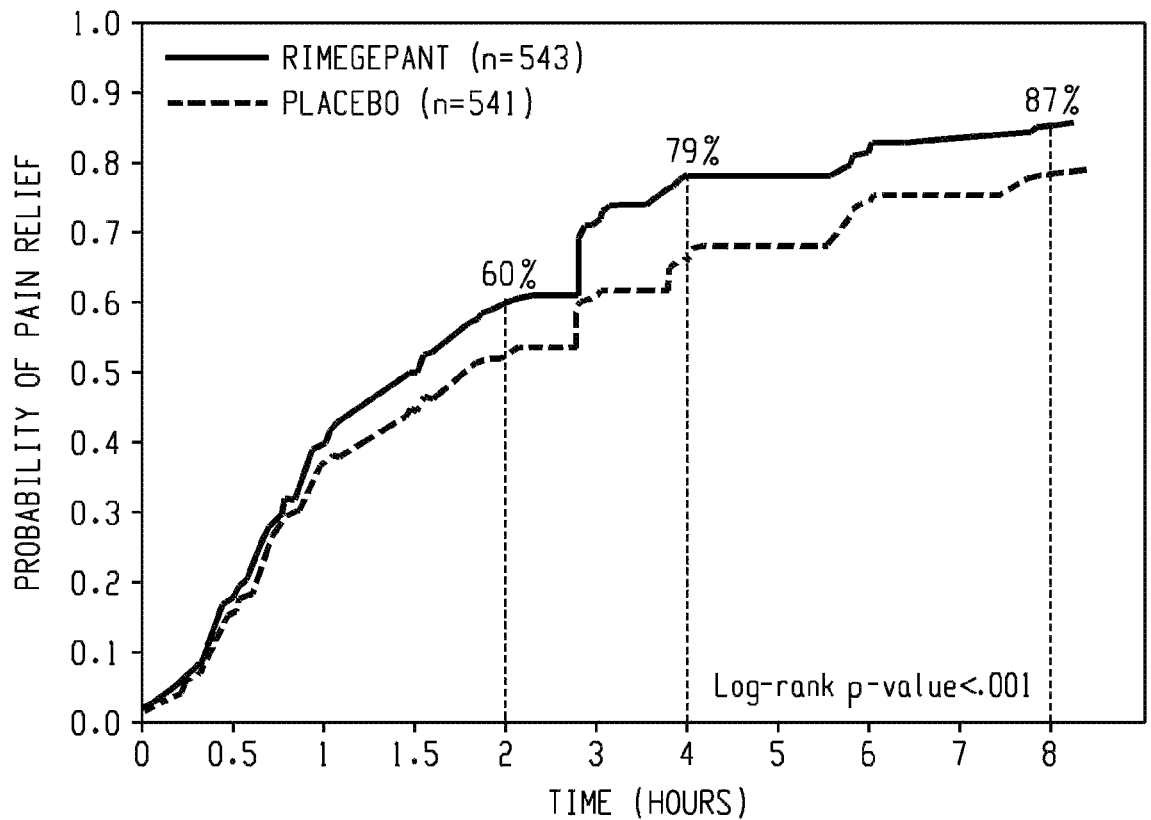
FIG. 3 shows the time to pain relief up to 8 hours pose dose in a clinical study entitled BHV3000-301: Phase 3: Double-Blind, Randomized, Placebo-Controlled, Safety and Efficacy Trial of BHV-3000 (Rimegepant) for the Acute Treatment of Migraine (ClinicalTrials.gov Identifier: NCT03235479).

MBS, most bothersome symptom
[a]Endpoints were tested hierarchically in the order shown at P = .05
Results from Example 6 are also shown in FIG. 3.

Example 7

Efficacy of Rimegepant—Results and analysis from the Clinical Trial—BHV3000-302 described in Example 3.

Objectives

To compare the efficacy, safety, and tolerability of rimegepant 75 mg oral tablet with placebo in the acute treatment of migraine in adults.

Methods

In a double-blind, randomized, placebo-controlled, multicenter study (Study 302, NCT03237845) adults≥18 years of age with at least a 1-year history of ICHD 3-beta migraine were eligible to participate. Following a 3- to 28-day screening period, subjects were randomized to receive rimegepant 75 mg or matching placebo and instructed to treat a single migraine attack with 1 dose of the blinded study drug (rimegepant or placebo) when headache pain reached moderate or severe intensity. The coprimary endpoints were pain freedom at 2 hours postdose and freedom from the most bothersome symptom (MBS) at 2 hours postdose. Safety assessments included adverse events (AEs), ECGs, vital signs, physical measurements, and routine laboratory tests, including assessment of liver function. Unless stated otherwise, values presented are mean±SD.

Results

In total, 1186 subjects were randomized to receive rimegepant (n=594) or placebo (n=592), and 1072 were evaluated for efficacy (rimegepant n=537, placebo n=535). Subjects had a mean age of 40.6±12.0 years, 88.7% were female, and by history had 4.6±1.8 attacks per month. At 2 hours postdose, rimegepant treated patients had higher pain free rates than placebo treated patients (19.6% vs 12.0%, P=0.0006), were more likely to be free of the MBS (37.6% vs 25.2%, P<0.0001); and had higher rates of pain relief (58.1% vs 42.8%, P<0.0001). A single dose of rimegepant, without the use of rescue medication, demonstrated superiority versus placebo for sustained pain freedom and pain relief from 2 through 48 hours postdose (P=0.0181 and P<0.0001, respectively). On a measure of functional disability, a greater proportion of rimegepant-treated patients achieved normal function at 2 hours (P<0.0001).

The safety and tolerability profiles of rimegepant were similar to placebo. The most common AEs were nausea (1.8%, 10/543 vs 1.1%, 6/543) and urinary tract infection (1.5%, 8/543 vs 1.1%, 6/543). Serum ALT or AST levels greater than the upper limit of normal (ULN) were seen in 2.4% (13/543) and 2.2% (12/543) of subjects treated with rimegepant and placebo, respectively. No subject in either treatment group had a transaminase level greater than 3 times ULN, and no bilirubin elevations greater than 2 times ULN were observed. Serious AEs (SAEs) were observed in 1 subject in the rimegepant group (back pain) and 2 subjects in the placebo group. No SAEs were determined to be related to the study drug.

Conclusions

Significant and durable clinical effects were seen with a single dose of rimegepant across multiple outcome measures, including, pain freedom, freedom from MBS, pain relief, and recovery of normal function. Rimegepant 75 mg oral tablet demonstrated favorable tolerability and safety, including a liver safety profile similar to placebo. These clinically meaningful results complement the benefits seen in Study 301. Rimegepant may ultimately offer patients a novel approach for the acute treatment of migraine.

| Endpoints | Rimegepant 75 mg | Placebo | P-value[a] |
|---|---|---|---|
| Coprimary | | | |
| Pain-free at 2 hours | 19.6% [105/537] | 12.0% [64/535] | .0006 |
| Free from MBS at 2 hours | 37.6% [202/537] | 25.2% [135/535] | <.0001 |
| Selected secondary | | | |
| Photophobia-free at 2 hours | 37.4% [183/489] | 22.3% [106/477] | <.0001 |
| Phonophobia-free at 2 hours | 36.7% [133/362] | 26.8% [100/374] | .0039 |
| Pain relief at 2 hours | 58.1% [312/537] | 42.8% [229/535] | <.0001 |
| Nausea-free at 2 hours | 48.1% [171/355] | 43.3% [145/336] | .2084 |
| Sustained pain relief, 2-24 hours | 42.6% [229/537] | 26.5% [142/535] | <.0001 |

Figure 4:
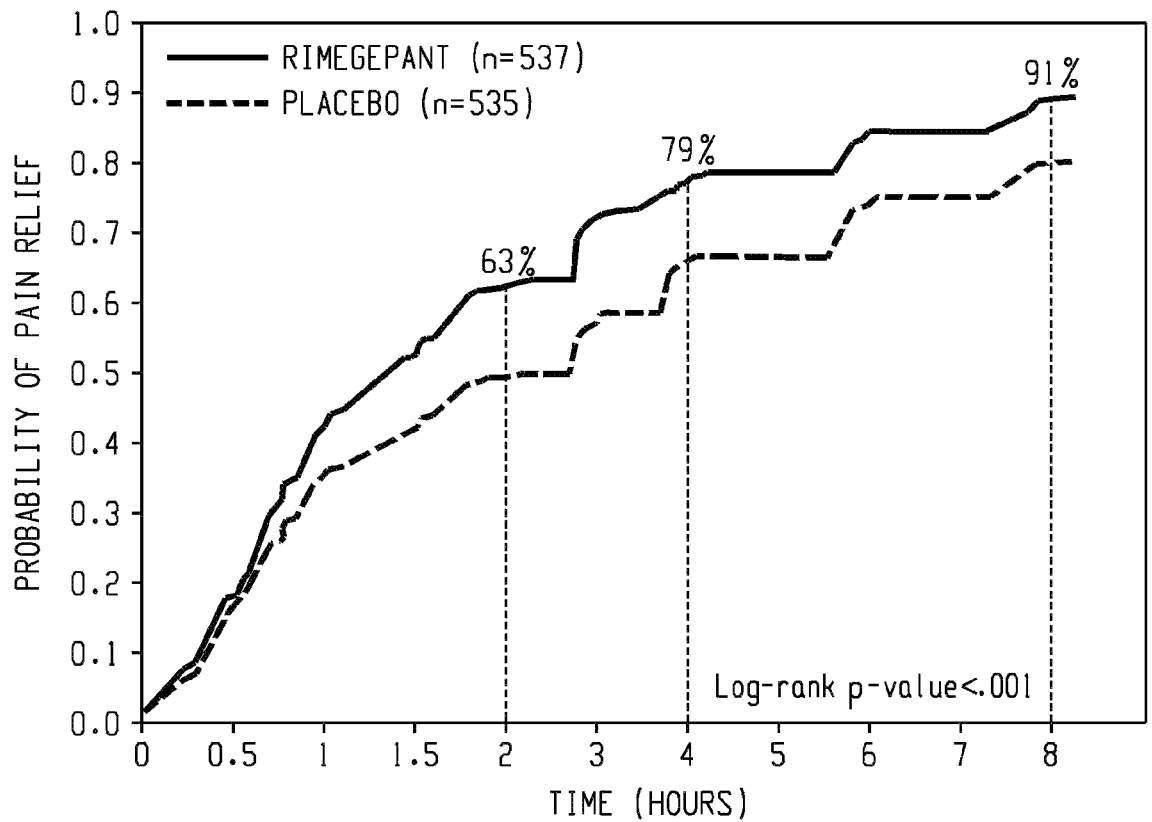
FIG. 4 shows the time to pain relief up to 8 hours pose dose in a clinical study entitled BHV3000-302: Phase 3: Double-Blind, Randomized, Placebo-Controlled, Safety and Efficacy Trial of BHV-3000 (Rimegepant) for the Acute Treatment of Migraine (ClinicalTrials.gov Identifier: NCT03237845).

MBS, most bothersome symptom
[a]Endpoints were tested hierarchically in the order shown at P = .05
Results from Example 7 are also shown in FIG. 4.

Example 8

Clinical Trial—BHV3000-303: Phase 3: Double-Blind, Randomized, Placebo-Controlled, Safety and Efficacy Trial of BHV-3000 (Rimegepant) Orally Discintegrating Tablet (ODT) for the Acute Treatment of Migraine (ClinicalTrials-.gov Identifier: NCT03461757)

A phase 3 clinical study was conducted with 1812 participants, as follows.
Study Description
Brief Summary:
The purpose of this study is to compare the efficacy of BHV-3000 (rimegepant ODT) versus placebo in subjects with Acute Migraines.

| Condition or disease | Intervention/treatment | Phase |
|---|---|---|
| Migraine | Drug: RimegepantDrug: Placebo | Phase 3 |

Study Design
Study Type: Interventional (Clinical Trial)
Actual Enrollment: 1812 participants
Allocation: Randomized
Intervention Model: Parallel Assignment
Masking: Triple (Participant, Care Provider, Investigator)
Primary Purpose: Treatment
Official Title: BHV3000-303: Phase 3, Double-Blind, Randomized, Placebo Controlled, Safety and Efficacy Trial of BHV-3000 (Rimegepant) Orally Disintegrating Tablet (ODT) for the Acute Treatment of Migraine
Actual Study Start Date: Feb. 27, 2018
Actual Primary Completion Date: Oct. 8, 2018
Actual Study Completion Date: Oct. 15, 2018
Arms and Interventions

| Arm | Intervention/treatment |
|---|---|
| Experimental: Arm 1: BHV-3000 (Active) | Drug: Rimegepant BHV-3000 (rimegepant) 75 mg (ODT) |
| Placebo Comparator: Arm 2: Placebo Comparator Drug | Drug: Placebo 75 mg matching placebo ODT |

Outcome Measures
Primary Outcome Measures:
1. Pain freedom of rimegepant compared with placebo in the acute treatment of migraine will be measured using the number of evaluable subjects that report no pain at 2 hours post-dose.
[Time Frame: Two hours post dose]
Pain will be measured on a 4 point Likert scale (0=none, 1=mild, 2=moderate, 3=severe)
2. Freedom from the most bothersome symptom (MBS) of rimegepant compared with placebo will be measured using the number of evaluable subjects that report the absence of their MBS at 2 hours post-dose. [Time Frame: Two hours post dose]
The MBS (nausea, phonophobia or photophobia) will measured using a binary scale (0=absent, 1=present).
Secondary Outcome Measures:
1. To measure rimegepant compared to placebo on Pain Relief, at 2 hours post-dose, that report a pain level of moderate or severe at baseline and then report a pain level of none or mild.
[Time Frame: 2 hours post-dose]
Pain Relief as measured by a 4 point numeric rating scale (None, Mild, Moderate, Severe)
2. Functional disability scale [Time Frame: 2 hour post-dose]
Subjects self-report "normal" on the functional disability scale
3. Rimegepant compared to placebo on sustained pain relief, from 2 to 24 hours by using the number of subjects that do not use any rescue medications, and do not experience any moderate or severe headache pain through that time. [Time Frame: 2 hours-24 hours post-dose]
Sustained Pain Relief as measured by a 4 point numeric rating scale (None, Mild, Moderate, Severe)
4. Sustained freedom from most bothersome symptom from 2 to 24 hours, assessed by using the number of subjects that do not experience their most bothersome symptom through below time period. [Time Frame: 2 to 24 hours post dose]
Most bothersome symptom
5. To measure rimegepant compared to placebo on the probability of requiring rescue medication will be assessed using the number of subjects that take rescue medication within 24 after administration of study medication (BHV3000 or placebo). [Time Frame: up to 24 hours post-dose]
Requiring Rescue Medication
6. Sustained ability to function at a normal level as measured by the Functional disability scale [Time Frame: 2 to 24 hours post dose]
Subjects self-report "normal" on the functional disability scale
7. Rimegepant compared to placebo on sustained pain relief from 2 to 48 hours, using the number of subjects that do not use any rescue medications and do not experience moderate to severe headache pain. [Time Frame: 2 hours-48 hours post-dose]
Sustained Pain Relief as measured by a 4 point numeric rating scale (None, Mild, Moderate, Severe)
8. Rimegepant compared to placebo on pain freedom from most bothersome symptom from 2-48 hours post dose. [Time Frame: 2 to 48 hours post dose]
Most bothersome symptom
9. Sustained ability to function at a normal level as measured by the Functional disability scale [Time Frame: 2 to 48 hours post dose]

Subjects self-report "normal" on the functional disability scale
10. Rimegepant compared to placebo by tabulating the number of subjects that report the absence of photophobia at 2 hours post-dose in the subset of subjects that reported the presence of photophobia at headache baseline [Time Frame: 2 hours post-dose]
Freedom from Photophobia
11. Functional disability scale [Time Frame: 90 minutes post dose]
Subjects self-report "normal" on the functional disability scale
12. Rimegepant compared to placebo on sustained pain relief at 90 minutes, using the number of subjects that do not use any rescue medications and do not experience moderate to severe headache pain. [Time Frame: 90 minutes post dose]
Pain Relief as measured by a 4 point numeric rating scale (None, Mild, Moderate, Severe)
13. Rimegepant compared to placebo from 2 to 24 hours, using the number of subjects that do not experience any headache pain through the time period of interest. [Time Frame: 2 hours-24 hours post-dose]
Sustained Pain Freedom as measured by a 4 point numeric rating scale (None, Mild, Moderate, Severe)
14. Sustained freedom from most bothersome symptom at 90 minutes, assessed by using the number of subjects that do not experience their most bothersome symptom through below time period. [Time Frame: 90 minutes post-dose]
Most bothersome symptom
15. Rimegepant compared to placebo on sustained pain freedom 90 minutes post dose, will be measured using the number of subjects that do not experience any headache pain through the time period of interest. [Time Frame: 90 minutes post-dose]
Sustained Pain Freedom as measured by a 4 point numeric rating scale
16. Rimegepant compared to placebo by tabulating the number of subjects that report the absence of phonophobia at 2 hours post-dose in the subset of subjects that reported the presence of phonophobia at headache baseline [Time Frame: 2 hours post-dose]
Freedom from Phonophobia
17. Rimegepant compared to placebo on sustained pain freedom, from 2 to 48 hours, will be measured using the number of subjects that do not experience any headache pain through the time period of interest. [Time Frame: 2 hours-48 hours post-dose]
Sustained Pain Freedom as measured by a 4 point numeric rating scale (None, Mild, Moderate, Severe)
18. To measure rimegepant compared to placebo on Pain Relief, at 60 minutes post-dose, that report a pain level of moderate or severe at baseline and then report a pain level of none or mild. [Time Frame: 60 minutes post dose]
Sustained Pain Relief as measured by a 4 point numeric rating scale (None, Mild; Moderate, Severe)
19. Functional disability scale [Time Frame: 60 minutes post dose]
Subjects self-report "normal" on the functional disability scale
20. Freedom from Nausea will by tabulating the number of subjects that report the absence of nausea at 2 hours post-dose in the subset of subjects that reported the presence of nausea at headache baseline. [Time Frame: 2 hours post-dose]
Freedom from Nausea
21. To assess the number of subjects that are pain free at 2 hours post-dose and then have a headache of any severity (response of 1, 2 or 3 on the 4-point scale within 48 hours after administrations of study medication, rimegepant or placebo. [Time Frame: 2 hours-48 hours post-dose]
Pain relapse
Further details concerning the clinical study including eligibility criteria, contacts and locations and more information can be found at www.clinicaltrials.gov for ClinicalTrials.gov NCT03461757.

Example 9

Figure 5:
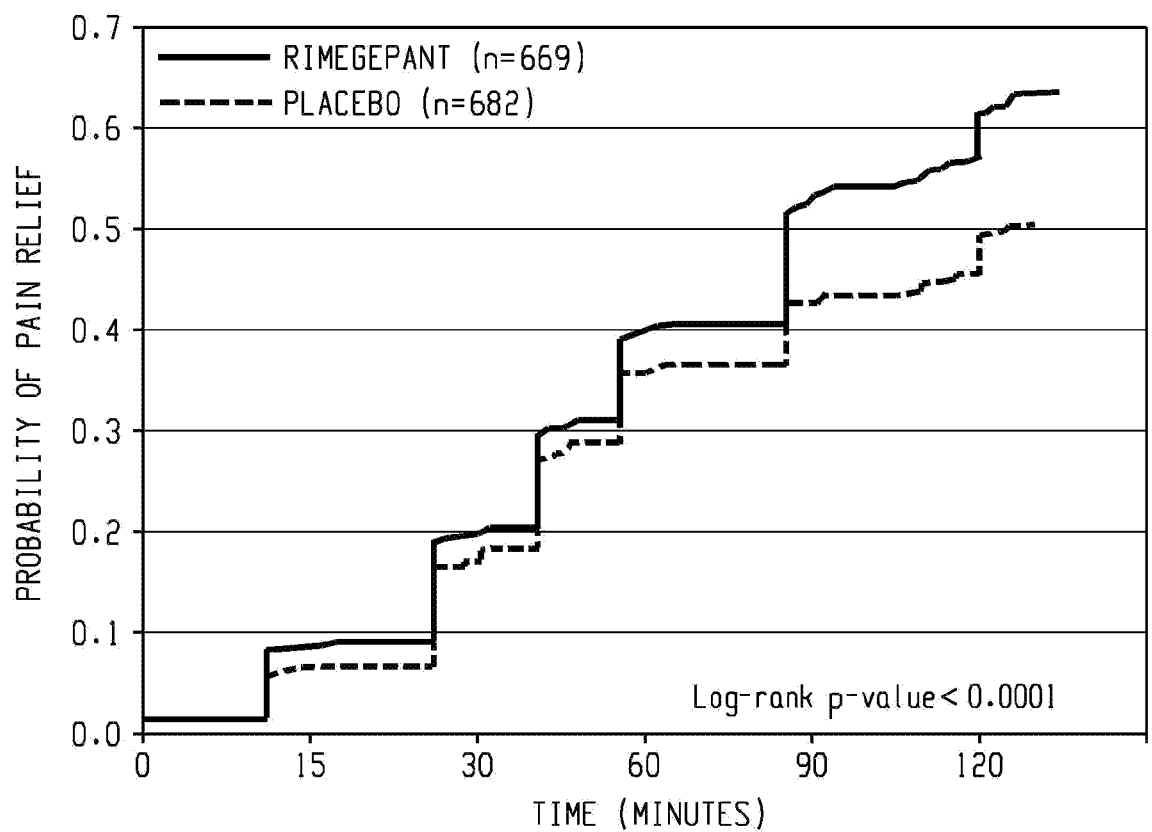
FIG. 5 shows a Kaplan-Meier pain relief curve through 2 hours after a single dose of rimegepant 75 mg Zydis ODT in a clinical study entitled BHV3000-303: Phase 3: Double-Blind, Randomized, Placebo-Controlled, Safety and Efficacy Trial of BHV-3000 20058-US-CON (Rimegepant) Orally Discintegrating Tablet (ODT) for the Acute Treatment of Migraine (ClinicalTrials.gov Identifier: NCT03461757).

Results from the clinical trial described in Example 8 are summarized as follows.
Study 303 met its co-primary registrational endpoints of pain freedom and freedom from most bothersome symptom (MBS) at 2 hours using a single dose (Table 8). Importantly, patients treated with the rimegepant Zydis ODT formulation in accordance with the present invention began to numerically separate from placebo on pain relief as early as 15 minutes and demonstrated statistical significance by 60 minutes ($p<0.0001$) (see FIG. 5). FIG. 5 shows the percentage of patients experiencing pain relief between 0 and 2 hours after dosing for patients who took a single dose of rimegepant Zydis ODT 75 mg or placebo. Data are Kaplan-Meier exploratory estimates with pain relief defined as patients who have either mild-pain or no-pain during the specified interval. Subjects were censored who took rescue medication or were lost to follow-up during the specified interval. Additionally, a significantly greater percentage of patients treated with rimegepant Zydis ODT returned to normal functioning within 60 minutes as compared to placebo ($p<0.002$). Lasting clinical benefit was observed through 48 hours on pain relief ($p<0.001$), pain freedom ($p<0.001$), most bothersome symptom ($p<0.001$), functional disability ($p<0.003$) and multiple other secondary endpoints after a single dose of rimegepant as compared to placebo. The vast majority of patients treated with rimegepant Zydis ODT (85%) did not use any rescue medications.

TABLE 8

Study 303
Pain Freedom & Freedom from Most Bothersome Symptom

| 2 Hour Endpoint | Rimegepant (N = 669) | Placebo (N = 682) | Difference | Adjusted p-value |
|---|---|---|---|---|
| Pain Freedom | 21.2% | 10.9% | 10.3% | <0.0001 |
| Freedom from MBS[1] | 35.1% | 26.8% | 8.3% | 0.0009 |

In Study 303, rimegepant Zydis ODT statistically differentiated from placebo on the two co-primary endpoints as well as the first 21 consecutive secondary outcome measures were prespecified in hierarchical testing (p-values<0.05). These secondary outcomes and additional exploratory outcome measures from this study are anticipated to be presented at upcoming scientific meetings in 2019.
The safety and tolerability of rimegepant in Study 303 was consistent with the profile previously observed in Study 301 (Example 2) and 302 (Example 3). Table 9 shows the pooled safety data across all three trials. No single adverse event (AE) occurred in the rimegepant group with an incidence higher than 1.6% and overall rates of AEs were similar to placebo. With regard to liver function tests, one patient treated with placebo and one patient treated with rimegepant showed LFTs>3×ULN in Study 303. Pooled liver function test results across the three pivotal trials (n=3,556) performed to date showed that rimegepant was similar to placebo with regard to aminotransferase (ALT or AST) levels above the upper limit of normal (ULN) and no patients experienced elevations in bilirubin>2×ULN (Table 10).

TABLE 9

Pooled Adverse Event (AE) Safety Data:
Complete Dataset of AEs from Studies 301, 302 and 303 of Patients Reporting an AE within 48 Hours Post-Dose ≥ 1% Incidence

| Adverse Event | Rimegepant (n = 1,771) | Placebo (n = 1,785) |
|---|---|---|
| ≥1 On-Study AE* | 252 (14.2%) | 209 (13.2%) |
| Nausea | 26 (1.5%) | 15 (0.8%) |
| UTI | 21 (1.2%) | 12 (0.7%) |
| SAEs** | 3 (0.2%) | 3 (0.2%) |

*No other individual AEs ≥ 1%, in rimegepant treated subjects, than listed in table. Includes all AEs without attribution to drug relatedness.
**No drug-related Serious Adverse Events (SAEs). 2 of the subjects with SAE in rimegepant group and 1 in placebo group had not been dosed before onset of SAE.

TABLE 10

Pooled Liver Function Test (LFT) Profile:
Complete Dataset of LFT Results from Studies 301, 302, and 303*

| ALT or AST | Rimegepant (n = 1,771) | Placebo (n = 1,785) |
|---|---|---|
| >ULN[1] | 48 (2.7%) | 52 (2.9%) |
| >3 × ULN | 2 (0.1%) | 2 (0.1%) |
| >5 × ULN | 1 (0.06%)[2] | 0 |
| >1 × ULN | 0 | 0 |
| >20 × ULN | 0 | 0 |

[1]Upper limit of normal; ALT alanine aminotransferase; AST aspartate aminotransferase
[2]AST elevation, Not Drug-Related as deemed by the investigator: subject newly initiated weight-lifting with laboratory results consistent with muscle injury
*AST/ALT Categories are not mutually exclusive; No bilirubin elevations > 2 × ULN across Studies 301, 302 and 303

Figure 6:
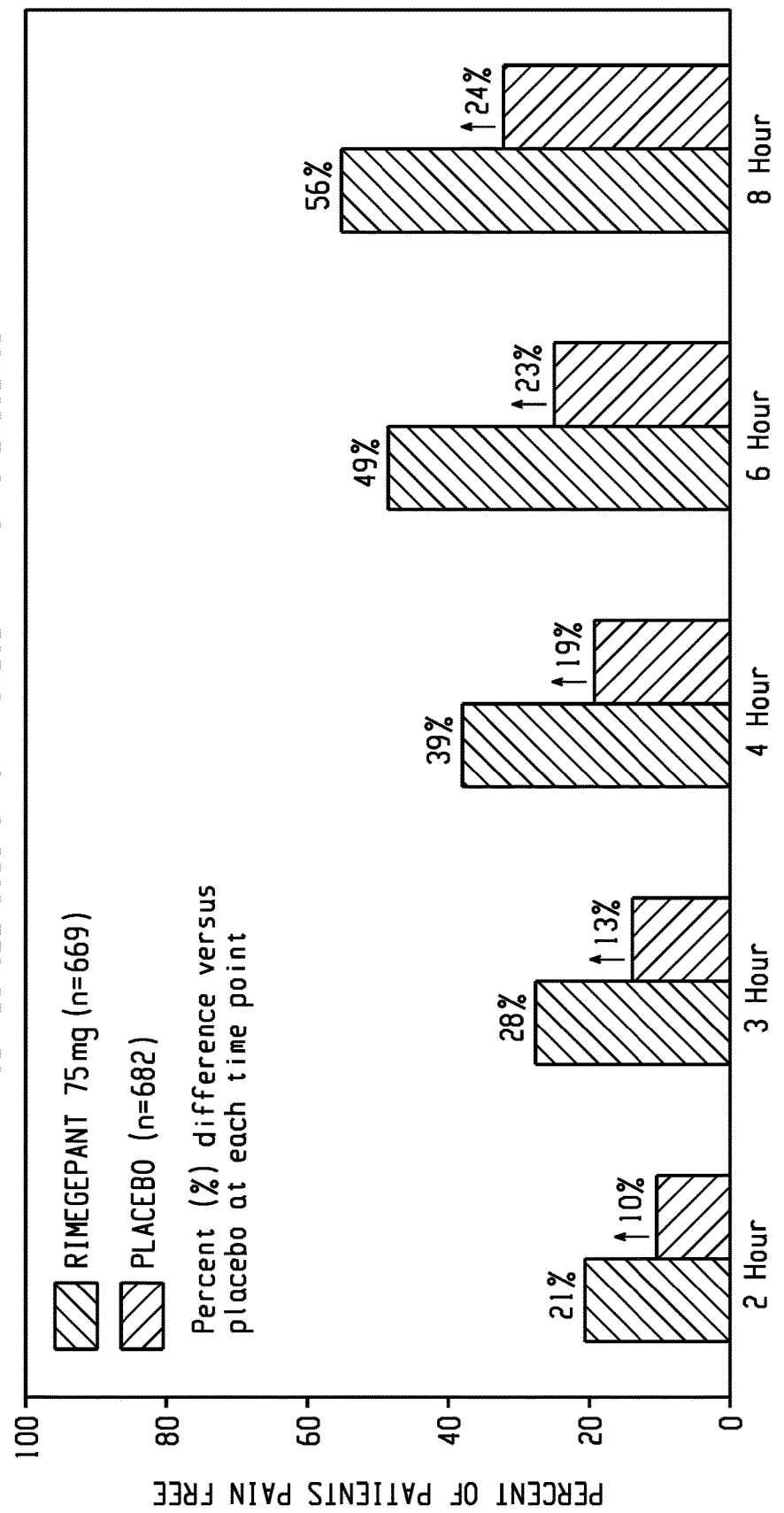
FIG. 6 shows a the pain free freedom from 2 to 8 hours after a single dose of rimegepant 75 mg Zydis ODT in a clinical study entitled BHV3000-303: Phase 3: Double-Blind, Randomized, Placebo-Controlled, Safety and Efficacy Trial of BHV-3000 (Rimegepant) Orally Discintegrating Tablet (ODT) for the Acute Treatment of Migraine (ClinicalTrials.gov Identifier: NCT03461757).

Further results from the clinical trial described in Example 8 (Study 303) are shown in Tables 11, 12 and FIG. 6.

TABLE 11

| ORDER | Primary Endpoints | Rimegepant | Placebo | P-value |
|---|---|---|---|---|
| Primary, 1 | Pain @ 2 hrs | 21.2% | 10.9% | <0.0001 |
| Primary, 2 | MBS @ 2 hrs | 35.1% | 26.8% | 0.0009 |

| SECONDARY ORDER | Secondary Endpoints | BHV | PBO | P-value |
|---|---|---|---|---|
| 1 | Pain Relief @ 2 hours | 59.3% | 43.3% | <0.0001 |
| 2 | Functional Disability at 2 hours | 38.1% | 25.8% | <0.0001 |
| 3 | SP Relief 2 to 24 hours | 47.8% | 27.7% | <0.0001 |
| 4 | MBS 2 to 24 | 27.1% | 17.7% | <0.0001 |
| 5 | Prob of Rescue Meds in 24 hours | 14.2% | 29.2% | <0.0001 |
| 6 | Functional Disability 2 to 24 | 29.6% | 16.9% | <0.0001 |
| 7 | SP Relief 2 to 48 hours | 42.2% | 25.2% | <0.0001 |
| 8 | MBS 2 to 48 | 23.2% | 16.4% | 0.0018 |
| 9 | Functional Disability 2 to 48 | 26.0% | 15.4% | <0.0001 |
| 10 | Photophobia @ 2 hours | 33.4% | 24.5% | 0.0007 |
| 11 | Functional Disabilty @ 90 minutes | 30.2% | 21.3% | 0.0002 |
| 12 | Pain Relief @ 90 minutes | 49.6% | 37.2% | <0.0001 |
| 13 | SP Freedom 2 to 24 hours | 15.7% | 5.6% | <0.0001 |
| 14 | MBS Freedom at 90 minutes | 27.4% | 21.5% | 0.0128 |
| 15 | Pain Freedom @ 90 minutes | 15.1% | 7.3% | <0.0001 |
| 16 | Phonophobia @ 2hours | 41.7% | 30.2% | 0.0003 |
| 17 | SP Freedom 2 to 48 hours | 13.5% | 5.4% | <0.0001 |
| 18 | Pain Relief at 60 minutes | 36.8% | 31.2% | 0.0314 |
| 19 | Functional Disability at 60 minutes | 22.3% | 15.8% | 0.0025 |
| 20 | Nausea @ 2 hours | 51.0% | 45.2% | 0.0898 |
| 21 | Pain Relpase 2 to 48 | 36.6% | 50.0% | 0.0577 |

TABLE 12

RIMEGEPANT (BHV-3000) PHASE 3-STUDY 303
Sustained Pain Relief[1] from 2, 3, & 4 to 24 or 48 hours

| | Sustained Pain Relief | Rimegepant n = 669 | Placebo n = 682 | p-value |
|---|---|---|---|---|
| 24 hr | 2 to 24 hrs | 47.8% | 27.7% | <0.001 |
| | 3 to 24 hrs | 56.4% | 33.1% | <0.001 |
| | 4 to 24 hrs | 61.7% | 36.8% | <0.001 |
| 48 hr | 2 to 48 hrs | 42.2% | 25.2% | <0.001 |
| | 3 to 48 hrs | 49.9% | 29.8% | <0.001 |
| | 4 to 48 hrs | 54.7% | 33.0% | <0.001 |

[1]Sustained Pain Relief is defined as patients who have either mild-pain or no-pain during the specified interval, with no use of rescue medication. Analyses of 3-24, 4-24, and 4-48 hours are exploratory.

Example 10

Clinical Trial—BHV3000-201: Open Label Safety Study in Acute Treatment of Migraine (ClinicalTrials.gov Identifier: NCT 03266588)
A phase ⅔ clinical study is conducted with about 2000 participants, as follows.
Study Description
Brief Summary:
The purpose of this study is to evaluate safety and tolerability of BHV3000 (rimegepant).

| Condition or disease | Intervention/treatment | Phase |
|---|---|---|
| Migraine | Drug: Rimegepant | Phase 2Phase 3 |

Study Design
   Study Type: Interventional (Clinical Trial)
   Estimated Enrollment: 2000 participants
   Intervention Model: Single Group Assignment
   Masking: None (Open Label)
   Primary Purpose: Treatment
   Official Title: A Multicenter, Open Label Long-Term Safety Study of BHV3000 in the Acute Treatment of Migraine
   Actual Study Start Date: Aug. 30, 2017
   Estimated Primary Completion Date: July 2019
   Estimated Study Completion Date: July 2019
Arms and Interventions

| Arm | Intervention/treatment |
|---|---|
| Experimental: Rimegepant | Drug: Rimegepant 75 mg oral tablet Other Name: BHV3000 |

Outcome Measures
Primary Outcome Measures:
1. To assess the safety and tolerability of rimegepant (BHV-3000) by measuring the frequency and severity of adverse events and discontinuations due to adverse events [Time Frame: 52 weeks] Number of subjects with treatment-emergent adverse events as assessed through laboratory tests, ECGs, physical exam findings (safety and tolerability)
Secondary Outcome Measures:
1. ALT or AST>3×ULN with total bilirubin>2×ULN [Time Frame: 52 weeks] elevated liver function tests
2. hepatic related adverse events and hepatic related adverse events that lead to discontinuation [Time Frame: 52 weeks] adverse events related to liver Further details concerning the clinical study including eligibility criteria, contacts and locations and more information can be found at www.clinicaltrials.gov for ClinicalTrials.gov Identifier: NCT03266588.

Example 11

Results from the clinical trial described in Example 10 are summarized as follows. Study BHV3000-201 demonstrated initial positive results. The interim analysis (database cutoff of Nov. 21, 2018) demonstrated that the safety and tolerability of long-term dosing of rimegepant in patients with migraine is consistent with the profile observed in phase 1-3 studies to date. Patients were allowed to treat migraine attacks of all severities (mild to severe) up to once daily for a full year. The initial results for hepatic safety and tolerability of rimegepant 75 mg in study participants is based upon review of both adverse events and regularly scheduled liver function tests. Interim hepatic data were reviewed by an external and independent panel of liver experts. There were no liver cases assessed as probably related to study drug and there were no Hy's Law cases identified. The panel concluded that there was no liver safety signal detected to date, including a subset of patients with near-daily dosing (≥15 doses/month). In the aggregate, it was noted that compared to migraine trials with drugs other than rimegepant, there was a very low incidence of overall elevations of liver function test abnormalities in rimegepant treated patients (1.0% incidence of serum ALT or AST>3× ULN). Subjects will continue to participate in Study 201 with additional data analyses to be submitted in the NDA and required 120-day safety updates.

In addition to the interim safety analysis, data from subjects was assessed to determine reductions in the number of headache days per month. The data presented in Table demonstrate that patients experienced fewer headache days per month while taking rimegepant during their treatment phase versus their observation phase of the study. For example, of 1731 subjects, 683 (39.5%) had a reduction in headache days per month of at least 20%, 602 (34.8%) had a reduction in headache days per month of at least 25%, 523 (30.2%) had a reduction in headache days per month of at least 30%, 442 (25.5%) had a reduction in headache days per month of at least 35%, 362 (20.9%) had a reduction in headache days per month of at least 40%, 287 (16.6%) had a reduction in headache days per month of at least 45%, 226 (13.1%) had a reduction in headache days per month of at least 50%. This result was surprising and unexpected and indicates that rimegepant may function as a preventative treatment for migraine as well as an acute treatment. Reductions in the mean number of headache days per month was observed beginning as early as the first month and continued in subsequent months of therapy.

Accordingly, in accordance with the present invention, it may be possible to treat patients that suffer from migraine headaches by administering rimegepant to the patient at a dosage, e.g., 75 mg, and at a frequency, e.g., once per month, twice per month, three times per month, four times per month, five or more times per month, ten or more times per month, fifteen or more times per month, effective to reduce the number of headaches per month, e.g., a 20% or greater reduction in the number.

TABLE 13

BHV-3000-201-Percent Decrease in Migraines per Month

| | Enrollment Group (2-8) | Enrollment Group (9-14) | Enrollment Group (4-14) | Overall |
|---|---|---|---|---|
| Overall Percent Decrease | | | | |
| n | 1004 | 458 | 269 | 1731 |
| >=20.0% decrease | 353 (35.2) | 171 (37.3) | 159 (59.1) | 683 (39.5) |
| >=25.0% decrease | 308 (30.7) | 150 (32.8) | 144 (53.5) | 602 (34.8) |
| >=30.0% decrease | 268 (26.7) | 125 (27.3) | 130 (48.3) | 523 (30.2) |
| >=35.0% decrease | 224 (22.3) | 101 (22.1) | 117 (43.5) | 442 (25.5) |
| >=40.0% decrease | 181 (18.0) | 81 (17.7) | 100 (37.2) | 362 (20.9) |
| >=45.0% decrease | 144 (14.3) | 60 (13.1) | 83 (30.9) | 287 (16.6) |
| >=50.0% decrease | 113 (11.3) | 46 (10.0) | 67 (24.9) | 226 (13.1) |

Throughout this application, various publications are referenced by author name and date, or by patent number or patent publication number. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

Those skilled in the art will recognize, or be able to ascertain using no more than routine experimentation, numerous equivalents to the specific procedures described herein. Such equivalents are considered to be within the scope of this invention and are covered by the following claims. For example, pharmaceutically acceptable salts other than those specifically disclosed in the description and Examples herein can be employed. Furthermore, it is intended that specific items within lists of items, or subset groups of items within larger groups of items, can be combined with other specific items, subset groups of items or larger groups of items whether or not there is a specific disclosure herein identifying such a combination.

What is claimed is:

1. A pharmaceutical composition comprising a pharmaceutically acceptable carrier and a therapeutically effective amount of a CGRP receptor antagonist, or a pharmaceutically acceptable salt thereof, wherein the pharmaceutical composition is in a form of an oral solid molded fast-dispersing dosage form.

2. The pharmaceutical composition of claim 1, wherein the CGRP receptor antagonist is selected from olcegepant, telcagepant, ubrogepant, atogepant, and rimegepant.

3. The pharmaceutical composition of claim 1, further comprising gelatin as a carrier.

4. The pharmaceutical composition of claim 1, further comprising mannitol as a filler.

5. The pharmaceutical composition of claim 1, comprising from about 70-80 weight % of the CGRP antagonist, about 10-20 weight % fish gelatin, about 10-20 weight % of a filler, and 0.1-5.0 weight % of a flavorant.

6. The pharmaceutical composition of claim 1, wherein the pharmaceutical composition is capable of disintegrating or dispersing within an interval selected from 1 to 60 seconds, 1 to 30 seconds, 1 to 10 seconds, and 2 to 8 seconds, after being placed in contact with a fluid.

7. The pharmaceutical composition of claim 6, wherein the fluid comprises saliva.

8. A method of treating migraine in a patient in need thereof, comprising administering to the patient a pharmaceutical composition comprising a pharmaceutically acceptable carrier and a therapeutically effective amount of a CGRP receptor antagonist, or a pharmaceutically acceptable salt thereof, wherein the pharmaceutical composition is in a form of an oral solid molded fast-dispersing dosage form.

9. The method of claim 8, wherein the CGRP receptor antagonist is selected from olcegepant, telcagepant, ubrogepant, atogepant, and rimegepant.

10. The method of claim 8, comprising from about 70-80 weight % of the CGRP antagonist, about 10-20 weight % fish gelatin, about 10-20 weight % of a filler, and 0.1-5.0 weight % of a flavorant.

11. A pharmaceutical composition comprising a pharmaceutically acceptable carrier and a therapeutically effective amount of rimegepant, or a pharmaceutically acceptable salt thereof, wherein the pharmaceutical composition is in a form of an oral solid molded fast-dispersing dosage form.

12. The pharmaceutical composition of claim 11, comprising about 75 mg of rimegepant or a pharmaceutically acceptable salt thereof.

13. The pharmaceutical composition of claim 11, wherein the rimegepant is in the form of a hemisulfate sesquihydrate salt.

14. The pharmaceutical composition of claim 11 in the form of a tablet.

15. The pharmaceutical composition of claim 11, that provides an $AUC_{0-t}$ of from about 80-125% of 5000 (hr*ng/mL).

16. The pharmaceutical composition of claim 11, comprising from about 70-80 wt % rimegepant hemisulfate sesquihydrate, about 10-20 wt % fish gelatin, about 10-20 wt % of a filler, and 0.1-5.0 wt % of a flavorant.

17. The pharmaceutical composition of claim 11, further comprising gelatin as a carrier.

18. The pharmaceutical composition of claim 11, further comprising mannitol as a filler.

19. The pharmaceutical composition of claim 11, wherein the pharmaceutical composition is capable of disintegrating or dispersing within an interval selected from 1 to 60 seconds, 1 to 30 seconds, 1 to 10 seconds, and 2 to 8 seconds, after being placed in contact with a fluid.

20. The pharmaceutical composition of claim 19, wherein the fluid comprises saliva.

* * * * *